US009539069B2

(12) United States Patent
Battula et al.

(10) Patent No.: US 9,539,069 B2
(45) Date of Patent: Jan. 10, 2017

(54) DENTAL IMPLANT WEDGES

(71) Applicant: Zimmer Dental, Inc., Carlsbad, CA (US)

(72) Inventors: Suneel Ranga Sai Battula, San Diego, CA (US); Hai Bo Wen, Carlsbad, CA (US); Eneetra Patrice Livings, Carlsbad, CA (US); Michael Scott Collins, San Marcos, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

(21) Appl. No.: 13/838,341

(22) Filed: Mar. 15, 2013

(65) Prior Publication Data
US 2013/0288200 A1    Oct. 31, 2013

Related U.S. Application Data

(60) Provisional application No. 61/638,667, filed on Apr. 26, 2012.

(51) Int. Cl.
*A61C 8/00* (2006.01)
(52) U.S. Cl.
CPC .............. *A61C 8/008* (2013.01); *A61C 8/006* (2013.01); *A61C 8/0018* (2013.01)
(58) Field of Classification Search
CPC ..... A61C 8/0006; A61C 8/0018; A61C 8/008; A61C 8/00
USPC ...... 433/148, 72–76, 149–189, 215; 424/9.1, 424/424; 623/17.7, 16, 11, 23.55; 514/2; 606/86, 53; 264/26; 427/2.24, 2
See application file for complete search history.

(56) References Cited

U.S. PATENT DOCUMENTS

| | | | |
|---|---|---|---|
| 2,112,007 A * | 3/1938 | Adams | 433/174 |
| 3,514,489 A | 5/1970 | Lemberg | |
| 3,579,829 A | 5/1971 | Sampson | |
| 3,855,638 A | 12/1974 | Pilliar | |
| 3,952,414 A * | 4/1976 | Shovers | A61C 8/0012 433/173 |
| 4,073,999 A | 2/1978 | Bryan et al. | |
| 4,121,340 A | 10/1978 | Patrick | |
| 4,379,694 A | 4/1983 | Riess | |
| 4,521,192 A | 6/1985 | Linkow | |
| 4,531,916 A * | 7/1985 | Scantlebury et al. | 433/173 |
| 4,702,697 A | 10/1987 | Linkow | |
| 4,957,439 A | 9/1990 | Shoher et al. | |
| 4,964,801 A | 10/1990 | Kawahara et al. | |
| 5,032,445 A | 7/1991 | Scantlebury et al. | |
| 5,052,930 A | 10/1991 | Lodde et al. | |
| 5,084,051 A | 1/1992 | Tormala et al. | |

(Continued)

OTHER PUBLICATIONS

"U.S. Appl. No. 13/954,051, Non Final Office Action mailed Mar. 26, 2014", 8 pgs.

(Continued)

*Primary Examiner* — Cris L Rodriguez
*Assistant Examiner* — Mirayda A Aponte
(74) *Attorney, Agent, or Firm* — Schwegman Lundberg & Woessner, P.A.

(57) ABSTRACT

A method for securing a dental implant within a dental bone cavity is disclosed. The method may include inserting a dental wedge into the dental bone cavity and allowing bone tissues to grow toward and at least partially surround the dental wedge. Dental implantation systems for implementing the method are also disclosed. The system can include a dental wedge adapted to be inserted into a dental bone cavity.

12 Claims, 20 Drawing Sheets

(56) References Cited

U.S. PATENT DOCUMENTS

| | | | |
|---|---|---|---|
| 5,108,432 A | 4/1992 | Gustavson | |
| 5,201,736 A | 4/1993 | Strauss | |
| D336,683 S | 6/1993 | Inoue et al. | |
| 5,222,987 A | 6/1993 | Jones | |
| 5,282,861 A | 2/1994 | Kaplan | |
| 5,306,149 A | 4/1994 | Schmid et al. | |
| 5,360,341 A | 11/1994 | Abramowitz | |
| 5,372,503 A * | 12/1994 | Elia | 433/215 |
| 5,380,328 A | 1/1995 | Morgan | |
| 5,397,235 A * | 3/1995 | Elia | 433/173 |
| 5,513,989 A | 5/1996 | Crisio | |
| 5,759,033 A * | 6/1998 | Elia | 433/173 |
| 5,769,637 A | 6/1998 | Morgan | |
| 5,769,898 A * | 6/1998 | Jisander | 424/423 |
| 5,906,489 A | 5/1999 | Khazzam et al. | |
| 6,030,218 A | 2/2000 | Robinson | |
| 6,050,819 A | 4/2000 | Robinson | |
| 6,080,161 A * | 6/2000 | Eaves et al. | 606/76 |
| 6,328,765 B1 | 12/2001 | Hardwick et al. | |
| 6,382,975 B1 * | 5/2002 | Poirier | A61C 1/084 |
| | | | 433/173 |
| 6,383,519 B1 * | 5/2002 | Sapieszko | A61C 8/0012 |
| | | | 424/401 |
| 6,402,518 B1 * | 6/2002 | Ashman | 433/215 |
| 6,409,764 B1 | 6/2002 | White et al. | |
| 6,840,770 B2 * | 1/2005 | McDevitt | 433/173 |
| 7,887,587 B2 | 2/2011 | Griffiths et al. | |
| 8,177,557 B2 | 5/2012 | Delmonico et al. | |
| 8,202,089 B2 | 6/2012 | Dacremont | |
| 8,357,201 B2 * | 1/2013 | Mayer et al. | 623/18.11 |
| 8,485,820 B1 | 7/2013 | Ali | |
| 2001/0012606 A1 * | 8/2001 | Unger | A61C 8/001 |
| | | | 433/173 |
| 2002/0110785 A1 * | 8/2002 | Ashman | 433/173 |
| 2003/0036801 A1 * | 2/2003 | Schwartz et al. | 623/23.63 |
| 2003/0125750 A1 * | 7/2003 | Zwirnmann et al. | 606/104 |
| 2004/0152046 A1 | 8/2004 | Minoretti et al. | |
| 2005/0033427 A1 | 2/2005 | Freilch | |
| 2005/0159754 A1 | 7/2005 | Odrich | |
| 2005/0273165 A1 | 12/2005 | Griffiths et al. | |
| 2006/0008773 A1 | 1/2006 | Liao | |
| 2006/0166169 A1 | 7/2006 | Dawood | |
| 2006/0287732 A1 * | 12/2006 | Pezeshkian | 623/17.17 |
| 2006/0292523 A1 | 12/2006 | Elian | |
| 2007/0231364 A1 | 10/2007 | Nishimoto et al. | |
| 2007/0269483 A1 * | 11/2007 | Elia | A61C 8/00 |
| | | | 424/424 |
| 2007/0269769 A1 | 11/2007 | Marchesi | |
| 2008/0095709 A1 * | 4/2008 | Ella | 424/9.1 |
| 2009/0048145 A1 * | 2/2009 | Hellerbrand et al. | 514/2 |
| 2009/0198284 A1 * | 8/2009 | Henry | 606/286 |
| 2010/0023057 A1 * | 1/2010 | Aeschlimann et al. | 606/246 |
| 2010/0036441 A1 * | 2/2010 | Procter | 606/329 |
| 2010/0161061 A1 | 6/2010 | Hunt | |
| 2010/0256773 A1 | 10/2010 | Thijs et al. | |
| 2011/0008754 A1 | 1/2011 | Bassett et al. | |
| 2011/0035024 A1 | 2/2011 | Malmquist et al. | |
| 2011/0224739 A1 * | 9/2011 | Wieland et al. | 606/329 |
| 2012/0156644 A1 | 6/2012 | Mckay | |
| 2012/0178042 A1 * | 7/2012 | Brodkin et al. | 433/6 |
| 2012/0244498 A1 * | 9/2012 | Hall | A61F 2/2803 |
| | | | 433/173 |
| 2013/0090742 A1 * | 4/2013 | Boiangiu | 623/23.61 |
| 2013/0123928 A1 * | 5/2013 | Mayer et al. | 623/18.11 |
| 2013/0164707 A1 | 6/2013 | Ali | |
| 2013/0274819 A1 | 10/2013 | Horvath | |
| 2013/0280675 A1 | 10/2013 | Ali | |
| 2014/0038132 A1 | 2/2014 | Willis et al. | |
| 2014/0099601 A1 | 4/2014 | Bassett et al. | |
| 2014/0272778 A1 | 9/2014 | Llop | |
| 2016/0038255 A1 | 2/2016 | Llop | |

OTHER PUBLICATIONS

"U.S. Appl. No. 13/954,051, Response filed Jun. 26, 2014 to Non Final Office Action mailed Mar. 26, 2014", 15 pgs.

"U.S. Appl. No. 14/040,414, Non Final Office Action mailed Apr. 2, 2014", 10 pgs.

"U.S. Appl. No. 14/040,414, Response filed Jun. 26, 2014 to Non Final Office Action mailed Apr. 2, 2014", 17 pgs.

"Zimmer CurV Pre-Shaped Collagen Membrane, The Latest in Ridge Augmentation Takes Shape", Surgical Technique Guide—Anterior, Zimmer Dental, (2012), 15 pgs.

"Zimmer CurV Pre-Shaped Collagen Membrane, The Latest in Ridge Augmentation Takes Shape", Zimmer Dental, (2011), 2 pgs.

"U.S. Appl. No. 13/954,051, Final Office Action mailed Dec. 4, 2014", 7 pgs.

"U.S. Appl. No. 14/040,414, Final Office Action mailed Dec. 4, 2014", 11 pgs.

"U.S. Appl. No. 13/954,041, Response filed Feb. 4, 2015 to Final Office Action mailed Dec. 4, 2014", 11 pgs.

"U.S. Appl. No. 14/040,414, Advisory Action mailed Feb. 27, 2015", 7 pgs.

"U.S. Appl. No. 14/040,414, Response filed Feb. 4, 2015 to Final Office Action mailed Dec. 4, 2014", 16 pgs.

"U.S. Appl. No. 14/040,414, Response filed Mar. 4, 2015 to Advisory Action mailed Feb. 27, 2015", 16 pgs.

"U.S. Appl. No. 14/040,414, Examiner Interview Summary mailed Jan. 26, 2016", 3 pgs.

"U.S. Appl. No. 14/040,414, Non Final Office Action mailed Oct. 23, 2015", 10 pgs.

"U.S. Appl. No. 14/040,414, Response filed Jan. 25, 2016 to Non Final Office Action mailed Oct. 23, 2015", 9 pgs.

"U.S. Appl. No. 14/040,414, Notice of Allowance mailed Oct. 7, 2016", 16 pgs.

* cited by examiner

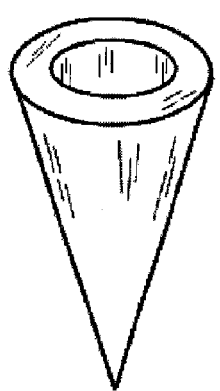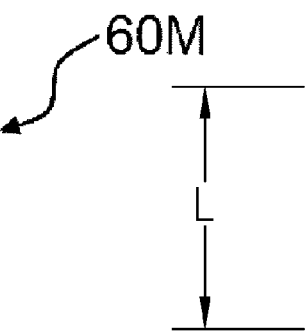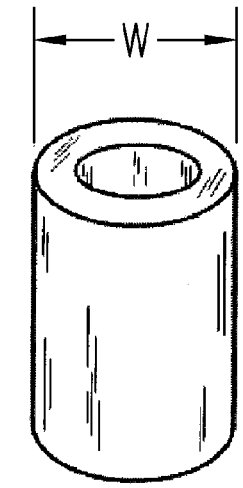
Fig.17  Fig.18
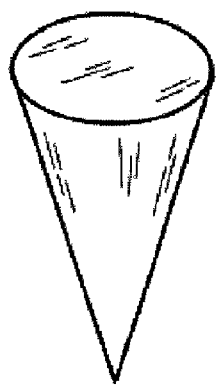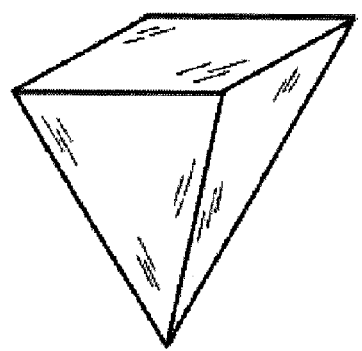
Fig.19  Fig.20
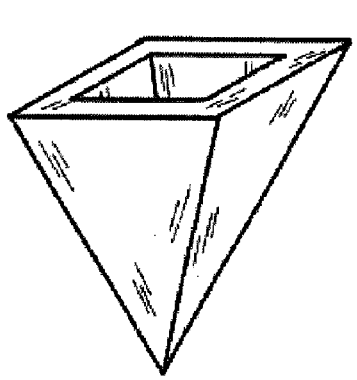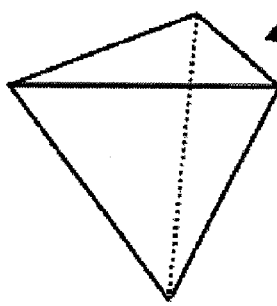
Fig.21  Fig.22

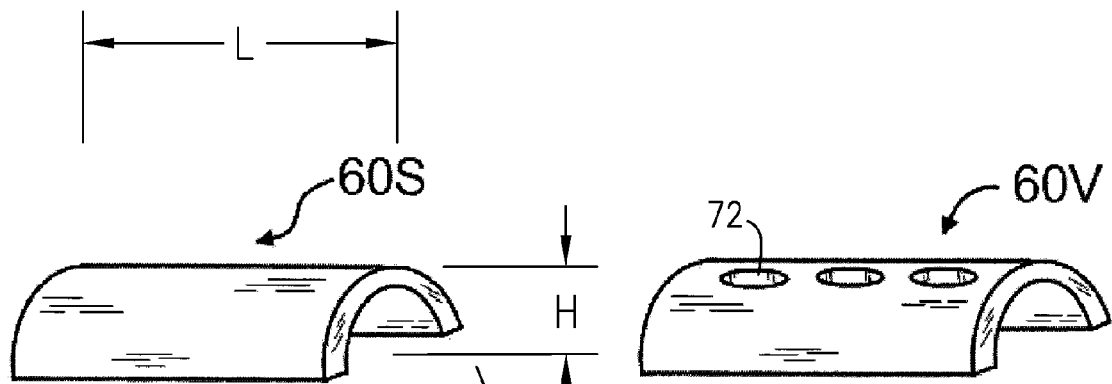
Fig.23　Fig.24
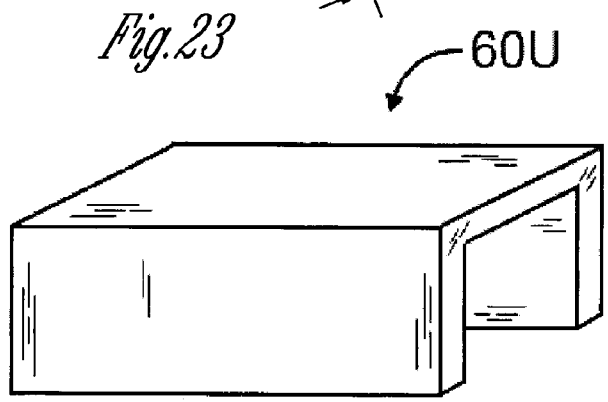 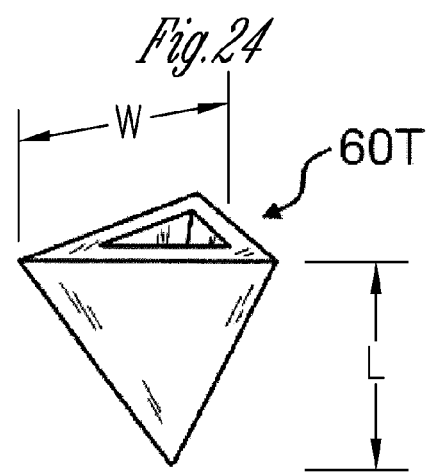
Fig.25　Fig.26
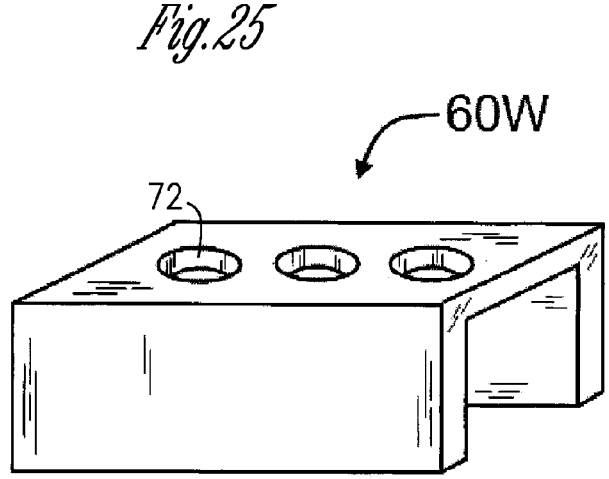 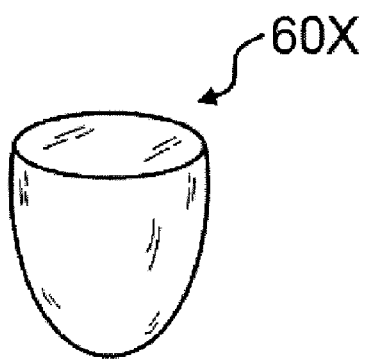
Fig.27　Fig.28

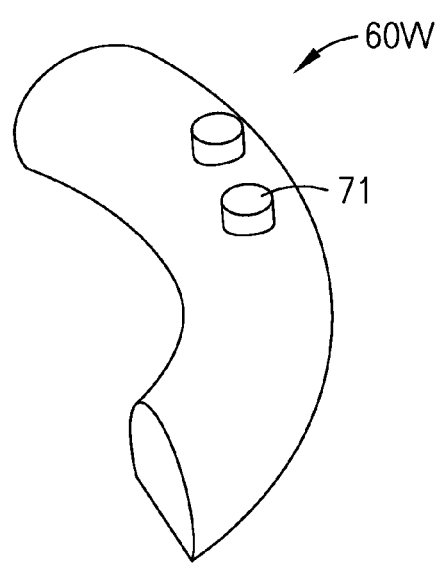
Fig.52
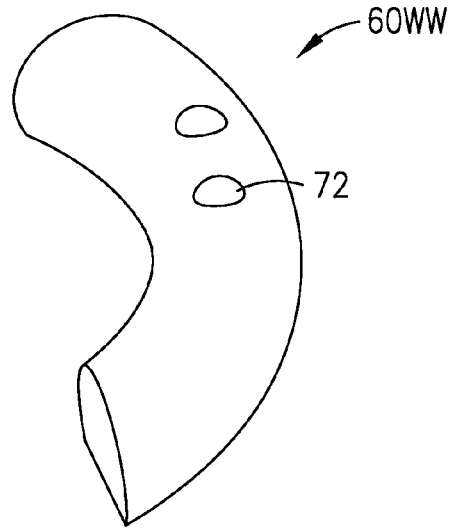
Fig.53
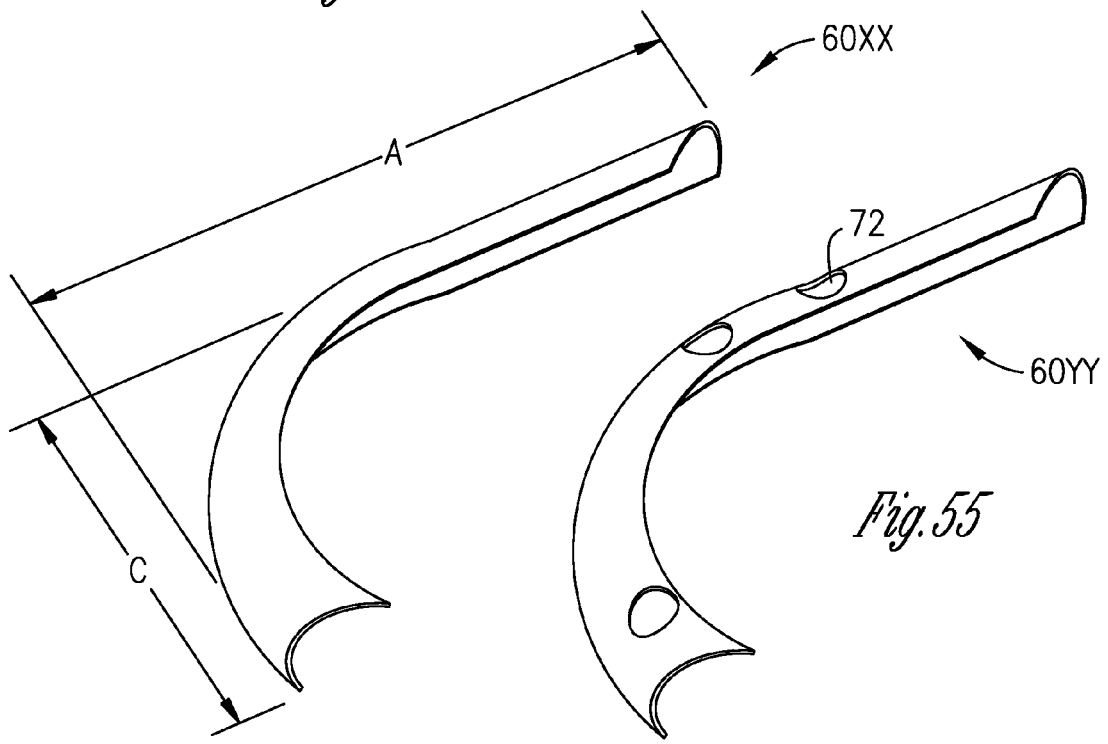
Fig.54
Fig.55

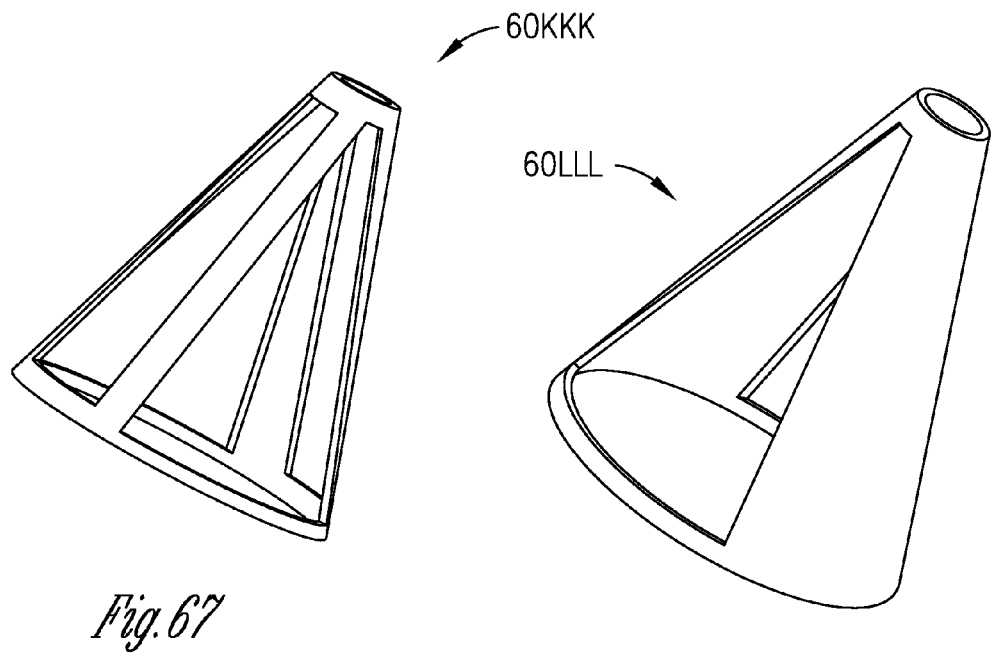
Fig. 67
Fig. 68
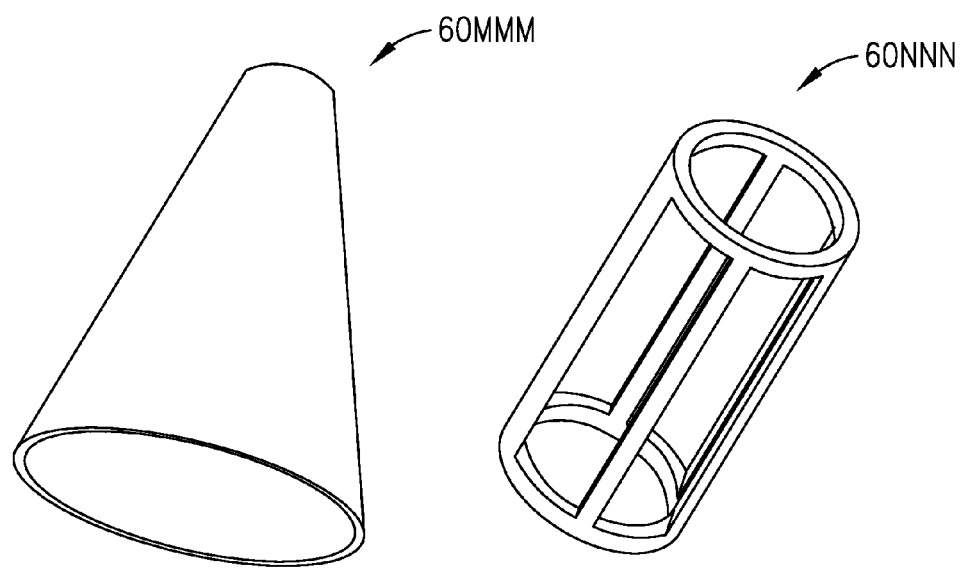
Fig. 69
Fig. 70

DENTAL IMPLANT WEDGES

CLAIM OF PRIORITY

This application claims the benefit of priority under 35 U.S.C. §119(e) of Battula, U.S. Provisional Patent Application Ser. No. 61/638,667, entitled "DENTAL IMPLANT SECUREMENT WEDGE", filed on Apr. 26, 2012, which is herein incorporated by reference in its entirety.

TECHNICAL FIELD

This disclosure generally relates to dental implants and, more particularly, relates to a wedge to provide securement, stability, or benefits to the dental implants.

BACKGROUND

Dental implants are commonly used in oral treatment procedures to restore appearance or function of lost or damaged teeth. Initial stability of the dental implantation can be difficult for patients with soft bone, patients suffering from osteo-disorders, or dental conditions associated with smoking or diabetes. Further, insufficient resistance or holding strength offered by the bone to stabilize the implant during or immediately after the surgery can increase dental implantation difficulties.

Various dental implants can mimic the root of the tooth that is intended to be replaced by the implants to increase stability. Those dental implants can include cylindrical exterior surfaces configured to be press fit into the dental bones, such as by inserting into an osteotomy created by a surgeon or inserting the implant in a cavity resulting from extraction of a tooth. More recently, self-tapping dental implants have been widely used to facilitate the insertion of the implant by creating threads in the dental bone as the implant is inserted. The threading process can lead to compaction of the bone around the threaded region of the implant to provide initial stability or to shield the bone from a load bearing activity during the healing process or osseointegration.

Though threaded implants can provide some initial stability, the outcome of the dental implantation can often depend on the quality of the dental bone into which the implant is inserted. For example, some bone can be soft or diseased and therefore unsuitable for threading. In addition, horizontal or vertical bone resorption can occur during the healing period after extraction. The resulting horizontal or vertical bone loss or weakening can lead to insufficient resistance or holding strength offered by the bone to stabilize the implant during or immediately after the implantation.

Bone augmentation, in which horizontal or vertical ridges are augmented prior to or after implantation can increase stability of dental bone. Existing methods for dental bone augmentation can include non-resorbable polytetrafluoroethylene (ePTFE) membranes with autograft, titanium mesh with particular grafts, forced tooth eruption, autogenous block grafting, or distraction oseteogenesis. Those methods can require up to about 12-16 weeks of bone healing or bone growth period, after which the implant can be placed at the intended location.

SUMMARY

The present inventors have recognized, among other things, that dental wedges, such as a bone augmentation wedge or an implant securement wedge, can be sized or shaped to better permit dental bone or tissue growth. For example, a dental wedge can be adapted to be inserted into dental cavity to permit tissue growth at least partially surrounding the wedge.

To better illustrate the dental wedges and related methods disclosed herein, a non-limiting list of examples is provided here:

In Example 1, a method for securing a dental implant within a dental bone cavity can comprise inserting a dental wedge into the dental bone cavity, allowing bone tissue to grow toward and at least partially surround the dental wedge, wherein the dental wedge is configured to enhance bone tissue growth, and maintaining at least one of a dental bone height and a dental bone width.

In Example 2, the method of Example 1 is optionally configured such that the dental wedge is at least one of a bone augmentation wedge and an implant securement wedge.

In Example 3, the method of any one or any combination of Examples 1-2 is optionally configured to further comprise inserting a dental implant through the dental wedge and contacting the dental implant with bone.

In Example 4, the method of any one or any combination of Examples 1-3 is optionally configured to further comprise inserting the dental implant proximate the dental wedge.

In Example 5, the method of any one or any combination of Examples 1-4 is optionally configured to further comprise locating the dental wedge within the bone tissues through a wedge locator In Example 6, the method of any one or any combination of Examples 1-5 is optionally configured such that the wedge locator is selected from a group consisting of X-ray apparatuses, CT scanners, CBCT scanners, and combinations thereof.

In Example 7, the method of any one or any combination of Examples 1-6 is optionally configured to further comprise providing bone graft material into the dental bone cavity.

In Example 8, the method of any one or any combination of Examples 1-7 is optionally configured to further comprise providing the bone graft material into the dental bone cavity before inserting the dental implant.

In Example 9, the method of any one or any combination of Examples 1-8 is optionally configured such that the dental wedge is made of a biocompatible material, the biocompatible material comprises at least one of a metal, a polymer, a ceramic, and combinations thereof, wherein the metal comprises at least one of titanium, trabecular metal, titanium alloy, tantalum, tantalum alloy, cobalt-chrome, and combinations thereof.

In Example 10, the method of any one or any combination of Examples 1-9 is optionally configured such that the dental wedge comprises a center bore.

In Example 11, a dental implantation system can comprise a dental wedge adapted to be inserted into a dental bone cavity, wherein the dental wedge is configured to substantially maintain at least one of a dental bone height and a dental bone width.

In Example 12, the dental implantation system of Example 11 is optionally configured to further comprise a wedge locator adapted to locate the dental wedge within the dental bone cavity and a dental implant adapted to be inserted into the dental bone cavity.

In Example 13, the dental implantation system of any one or any combination of Examples 11-12 is optionally configured to further comprise a dental bone augmentation composition adapted to allow bone tissues to grow toward and at least partially surround the dental wedge.

In Example 14, the dental implantation system of any one or any combination of Examples 11-13 is optionally configured such that the wedge locator is selected from a group consisting of X-ray apparatuses, CT scanners, CBCT scanners, and combinations thereof.

In Example 15, the dental implantation system of any one or any combination of Examples 11-14 is optionally configured to further comprise a guide operatively associated with the dental implant, the guide corresponding to the location of the dental wedge and adapted to align the dental implant with the dental wedge.

In Example 16, the dental implantation system of any one or any combination of Examples 11-15 is optionally configured such that the dental bone augmentation composition comprises a bone graft material.

In Example 17, the dental implantation system of any one or any combination of Examples 11-16 is optionally configured such that the dental wedge is made of a biocompatible material, the biocompatible material comprising at least one of a metal, a polymer, a ceramic, and combinations thereof, wherein the metal comprises at least one of titanium, trabecular metal, titanium alloy, tantalum, tantalum alloy, cobalt-chrome, and combinations thereof.

In Example 18, the dental implantation system of any one or any combination of Examples 11-19 is optionally configured such that wherein the dental wedge comprises a center bore.

In Example 19, the dental implantation system of any one or any combination of Examples 11-18 is optionally configured such that the dental wedge maintains a space within the dental bone cavity for the dental implant.

In Example 20, the dental implantation system of any one or any combination of Examples 11-19 is optionally configured such that the dental implant is inserted proximate the dental wedge.

In Example 21, the dental implantation system of any one or any combination of Examples 11-20 is optionally configured such that the dental implant is inserted into the dental wedge.

In Example 22, the dental implantation system of any one or any combination of Examples 11-21 is optionally configured such that after the dental wedge is inserted, the dental wedge changes to a form which provides enhanced stability for the dental implant.

In Example 23, the dental implantation system of any one or any combination of Examples 11-22 is optionally configured such that the dental wedge is configured to split within the dental cavity.

In Example 24, the dental implantation system or method of any one or any combination of Examples 1-23 is optionally configured such that all elements or options recited are available to use or select from.

These and other examples and features of the present tibial baseplates and methods will be set forth in part in the following Detailed Description. This Summary is intended to provide non-limiting examples of the present subject matter—it is not intended to provide an exclusive or exhaustive explanation. The Detailed Description below is included to provide further information about the dental wedges and methods

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 17 is a perspective view of an alternative form of a dental wedge, in accordance with at least one example.

FIG. 18 is a perspective view of an alternative form of a dental wedge, in accordance with at least one example.

FIG. 19 is a perspective view of an alternative form of a dental wedge, in accordance with at least one example.

FIG. 20 is a perspective view of an alternative form of a dental wedge, in accordance with at least one example.

FIG. 21 is a perspective view of an alternative form of a dental wedge, in accordance with at least one example.

FIG. 22 is a perspective view of an alternative form of a dental wedge, in accordance with at least one example.

FIG. 23 is a perspective view of an alternative form of a dental wedge, in accordance with at least one example.

FIG. 24 is a perspective view of an alternative form of a dental wedge, in accordance with at least one example.

FIG. 25 is a perspective view of an alternative form of a dental wedge, in accordance with at least one example.

FIG. 26 is a perspective view of an alternative form of a dental wedge, in accordance with at least one example.

FIG. 27 is a perspective view of an alternative form of a dental wedge, in accordance with at least one example.

FIG. 28 is a perspective view of an alternative form of a dental wedge, in accordance with at least one example.

FIG. 52 is a perspective view of an alternative form of a dental wedge, in accordance with at least one example.

FIG. 53 is a perspective view of an alternative form of a dental wedge, in accordance with at least one example.

FIG. 54 is a perspective view of an alternative form of a dental wedge, in accordance with at least one example.

FIG. 55 is a perspective view of an alternative form of a dental wedge, in accordance with at least one example.

FIG. 67 is a perspective view of an alternative form of a dental wedge, in accordance with at least one example.

FIG. 68 is a perspective view of an alternative form of a dental wedge, in accordance with at least one example.

FIG. 69 is a perspective view of an alternative form of a dental wedge, in accordance with at least one example.

FIG. 70 is a perspective view of an alternative form of a dental wedge, in accordance with at least one example.

DETAILED DESCRIPTION

Figure 1:
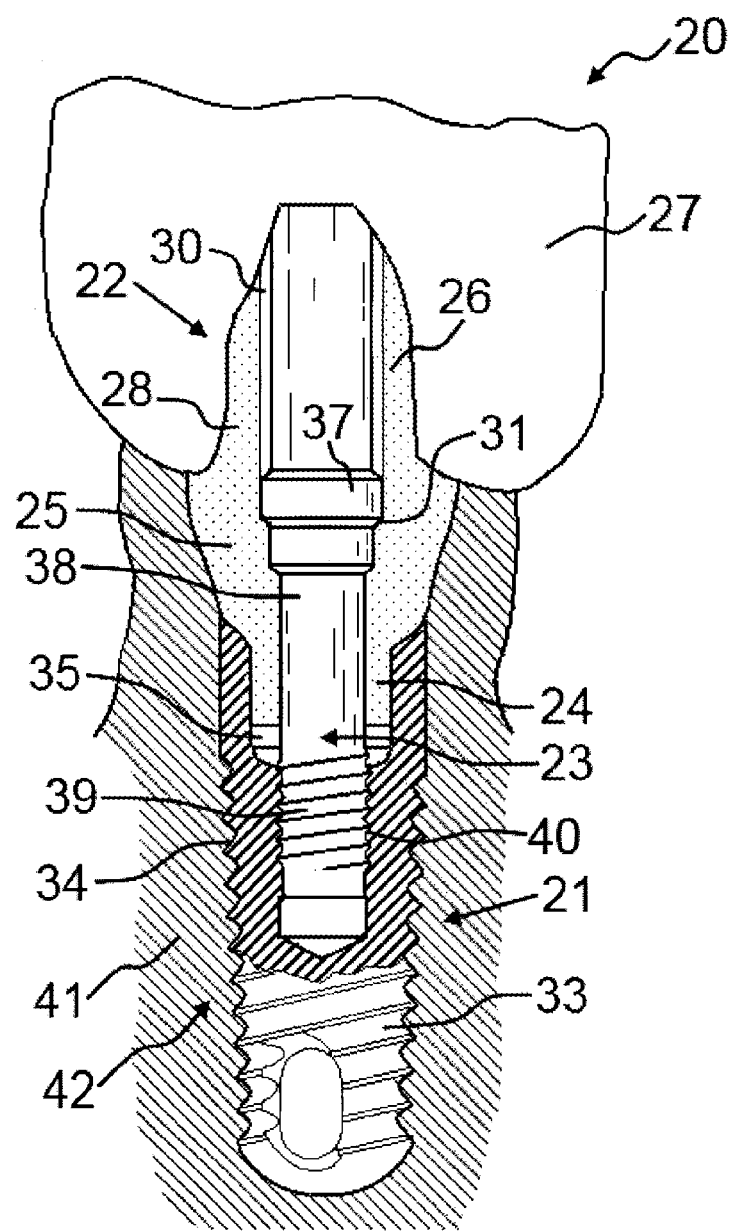
FIG. 1 is a cross-sectional view of a dental prosthetic apparatus with a dental implant inserted into a dental bone cavity, in accordance with at least one example.

As illustrated in FIG. 1, a dental prosthetic apparatus 20 can include a dental implant 21, an abutment 22, and a connector 23 interconnecting the dental implant and abutment (21, 22) to provide an anchor for a prosthetic tooth at an edentulous site in a dentition of a patient where a natural tooth has been lost or damaged. The abutment 22 can include a base portion 24 adapted to be mated with the dental implant 21. Further, a transgingival portion 25 can be adapted to extend through soft gingival tissue. A supragingival portion 26 can be adapted to extend beyond the transgingival portion 25 such that a prosthetic tooth or crown 27 can be attached. The abutment 22 can include a body 28 made of a suitable material, such as aluminum oxide, zirconium oxide, titanium, titanium alloy, or a combination thereof. The body 28 of the abutment 22 can define a center bore 30. The bore 30 can include a step 31 for engaging, such as by abutting, the connector 23 to secure the abutment 22 to the dental implant 21, as described herein.

The dental implant 21 can include a longitudinally extending body 33 adapted to be implanted into a cavity 42 formed in a dental bone 41 of a patient according to known surgical techniques. The body 33 of the dental implant 21 can include an exterior surface 34 for interacting with bone tissue, such that the dental implant 21 can be secured to the dental bone 41, such as through osseointegration or other biological or mechanical interactions. The body 33 can also include a center bore 35 in which the base portion 24 of the abutment 22 is inserted.

As illustrated in FIG. 1, the connector 23 can be provided in the dental prosthetic apparatus 20 for securing the abutment 22 to the dental implant 21. The connector 23 can include a head 37 or a shank 38 extending from the head 37, such that the shank can terminate into a threaded tail 39. In use, the connector 23 can be inserted through the center bore 30 of the abutment 22, and the tail 39 of the connector 23 can be threaded into an internally threaded region 40 of the center bore 35 of the dental implant 21 until the head 37 of the connector 23 abuts the step 31 of the center bore 30 of the abutment 22.

Figure 2:
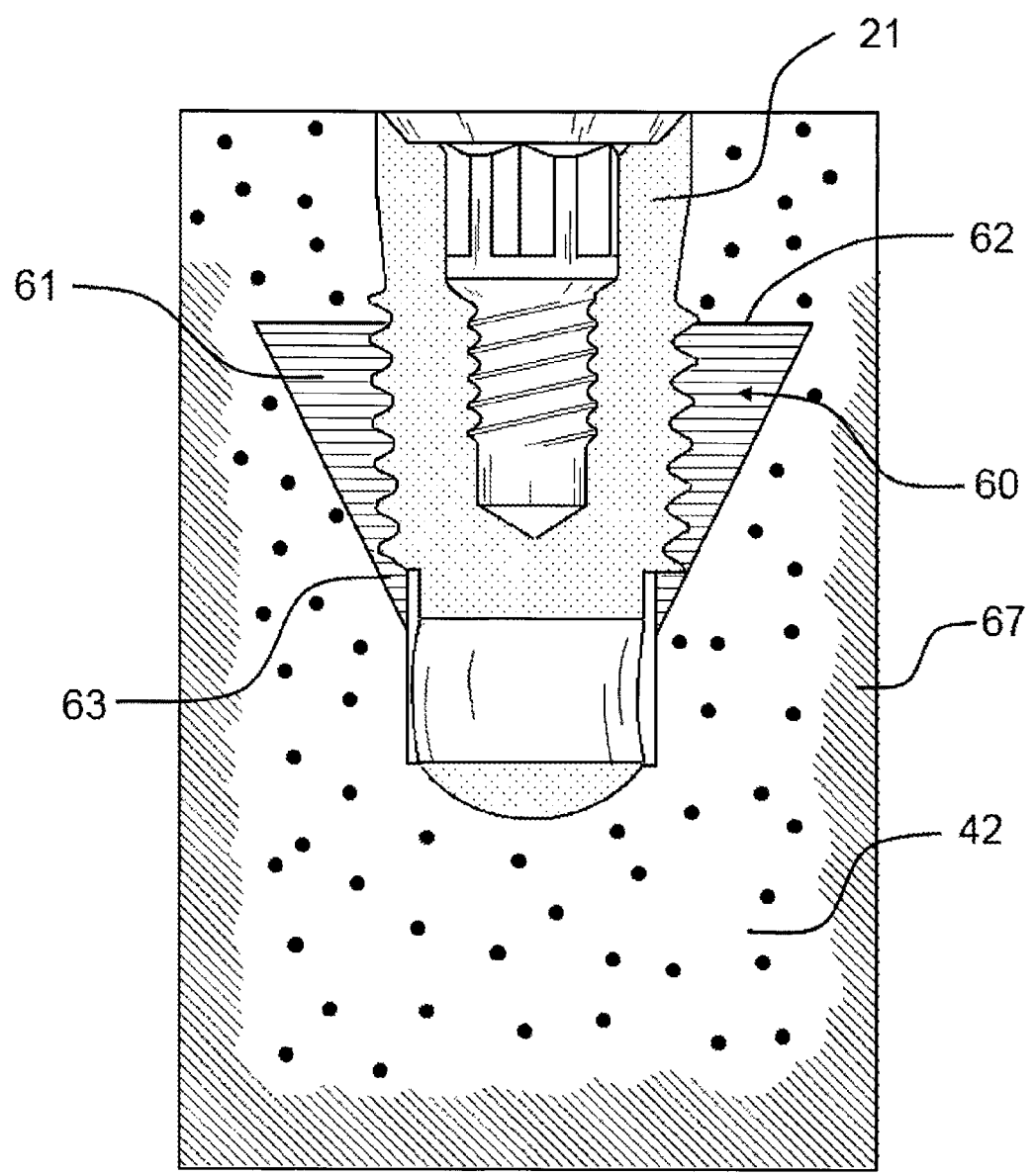
FIG. 2 is a cross-sectional view of a dental wedge suitable for use with the dental implant in FIG. 1, in accordance with at least one example.

FIG. 2 illustrates a cross-sectional view of a dental wedge 60 suitable for use with the dental implant 21. The dental wedge 60 can include a body 61 having a coronal end 62 and an apical end 63. The dental implant 21 can be inserted within the dental bone cavity 42 by inserting a dental wedge 60 into the dental bone cavity 42, allowing bone tissues to grow toward or at least partially surround the dental wedge 60, and inserting the dental implant 21 through the dental wedge 60 and into the dental bone cavity. Because the dental implant 21 and the dental wedge 60 can be fixedly attached together, the dimension, shape, or other structural features of the dental wedge 60 can contribute to the stability of the implant 21 within the dental bone cavity 42.

The dental wedge 60 can include a bone augmentation wedge or an implant securement wedge. For example, the dental wedge 60 can be configured to be inserted or implanted directly into dental bone, such as a bone augmentation wedge, or can be configured to be inserted in or proximate an implant wedge, such as an implant securement wedge. Further, the dental wedge 60 can be a combination of a bone augmentation wedge and an implant securement wedge.

In various examples, the dental wedge 60 can be inserted into the dental bone cavity 42, allowing bone tissues to grow toward or at least partially surround the dental wedge 60, such that the dental implant 21 can be inserted into the dental bone cavity 42 above, alongside, near, or proximate the dental wedge 60. Because the dental wedge 60 can permit or help bone grow toward or around it, the dimension, shape, or other structural features of the dental wedge 60 can contribute to the stability of the implant 21 within the dental bone cavity 42.

Figure 3:
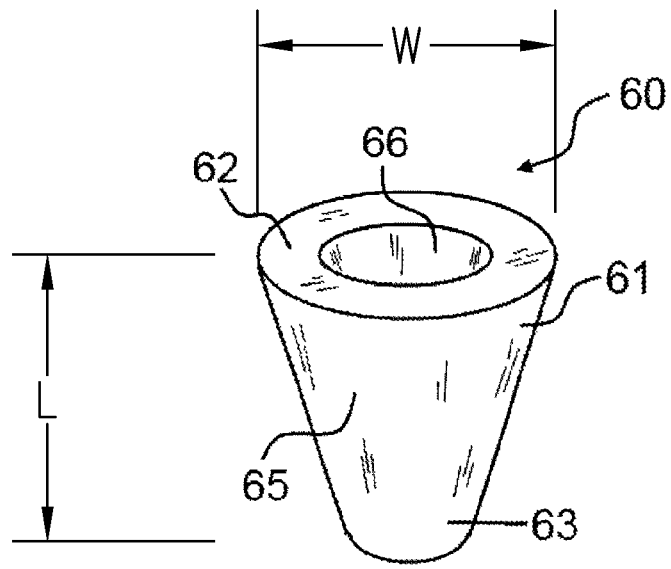
FIG. 3 is a perspective view of the dental wedge in FIG. 2, in accordance with at least one example.

FIG. 3 is a perspective view of a dental wedge 60 which can include a body 61 extending from a coronal end 62 to an apical end 63. At least a portion of the body 61 can be laterally thicker, such as a greater lateral width W than the implant 21 (FIGS. 1-2). The lateral width W can include a diameter, such as shown in FIG. 3. Further, the lateral length W can include a diagonal length of a square or rectangular cross-section or surface. In various examples, the body 61 can be tapered from the coronal end 62 to the apical end 63 along a length L. For example, the tapering shape can contribute to the stability of the dental wedge 60 or implant 21 within the dental bone cavity 42 (FIGS. 1-2). Generally, the coronal end 62 can be the end that is inserted first into the dental bone cavity 42, wherein the apical end 63 can be disposed toward a gum line. In various examples, the dental wedge 60 can be inserted in the dental bone cavity 42 or implant 21 within the maxilla or mandible. Further, a dental bone cavity 42, although shown as a single tooth cavity, is not so limited. It is contemplated that the dental bone cavity 42 can include the cavity formed by one tooth, a plurality of teeth, or the entire maxilla or mandible.

The dental wedge 60 can be made of the same material, such as a biocompatible material, as the implant 21 (FIGS. 1-2), or it can be made of a different material. For example, the dental wedge 60 can be made of titanium, trabecular metal, titanium alloy, tantalum, tantalum alloy, cobalt-chrome, or a combination thereof. Alternatively, the dental wedge 60 can be made of other stiff materials, such as slow resorbing biocompatible ceramic, resorbable biocompatible polymer, or a combination thereof. Further, the dental wedge 60 can be made of a composite of various biocompatible materials. In various examples, when the dental wedge 60 is made of titanium, the body 61 can include a porous exterior surface 65, such as through hydroxyappetite blasting. The porous exterior surface of the dental wedge 60 can facilitate osseointegration between bone tissue and the dental wedge 60, thereby further improving stability of the dental wedge 60 or implant 21 within the dental bone cavity 42 (FIGS. 1-2). The dental wedge 60 can, for example, be completely porous. That is, the exterior surface, as well as the body of the dental wedge 60 can be porous. In an example, the dental wedge can be solid, such as non-porous. Further, the dental wedge 60 can be any combination of porous and non-porous materials, such as a porous exterior surface; a porous slot surface, bore surface (e.g., inner exposed surface of the dental wedge), or protrusion surface; a solid body; a porous body; a solid exterior surface; or any combination thereof.

Figure 4:
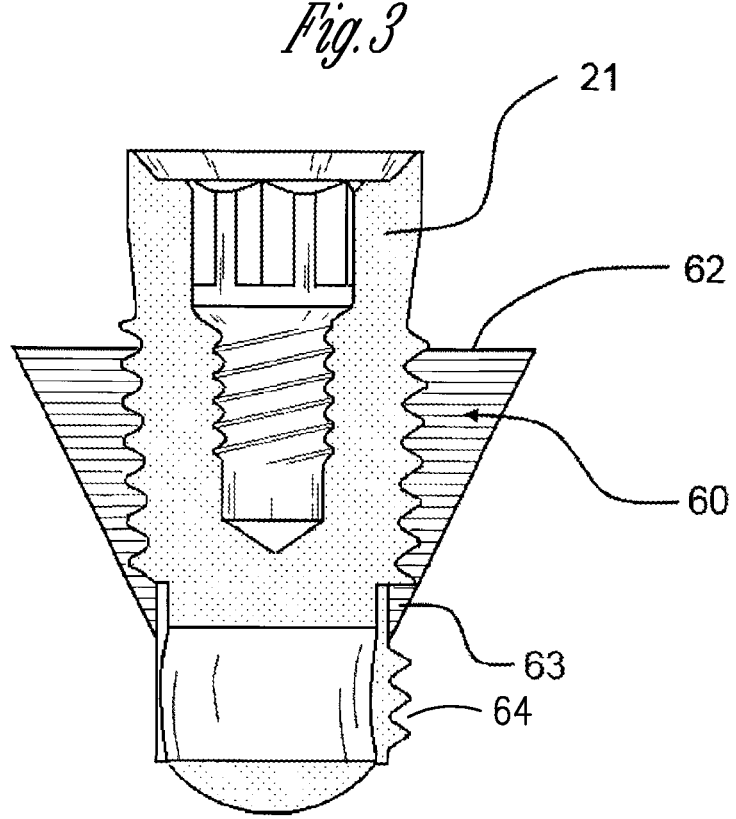
FIG. 4 is a cross-sectional view of the dental wedge and dental implant in FIG. 2, in accordance with at least one example.

The body 62 can include a center bore 66. The center bore 66 can extend from about the coronal end 62 to about the apical end 63. For example, the center bore 66 can define an opening at the coronal end 62. The center bore 66 can have an inner or outer diameter smaller than the outer diameter of the dental implant 21. As illustrated in FIG. 4, the center bore 66 can be used to guide the dental implant 21 to thread through the dental wedge 60, such that a secure self-tap fitment 64 is formed therebetween.

As described herein, the body 62 of the dental wedge 60, such as for a root augmentation application, can include a lateral width W and length L. For an anterior maxilla dental wedge 60, the lateral width W can be from about 0.5 millimeters (mm) to about 10 mm. Further, the lateral width W for a posterior maxilla dental wedge 60 can be from about 0.5 mm to about 12 mm. An anterior mandible dental wedge 60, according to the present disclosure, can have a lateral width W from about 0 5 mm to about 9 mm and a posterior mandible dental wedge 60 can include a lateral width W from about 0 5 mm to about 13 mm. Further, similar shaped dental wedges described herein can include similar length and width dimensions. Specifically, FIGS. 3, 15, 18, 23, 26, and 63 can have substantially similar length L and width W dimensions as described herein.

The length L of the dental wedge 60 can, for example, be from about 0.5 mm to about 19 mm for a maxilla anterior application, and from about 0.5 mm to about 15 mm for a maxilla posterior application. Further, the length L for a mandible anterior application can be from about 0.5 mm to about 19 mm and for a posterior mandible application from about 0.5 mm to about 17 mm.

As described herein, a hollow cavity or bore of the dental wedge can be filled with biomaterial or graft material, such that the dental wedge can be used for ridge augmentation or ridge bone height preservation or rebuilding.

Figure 5:
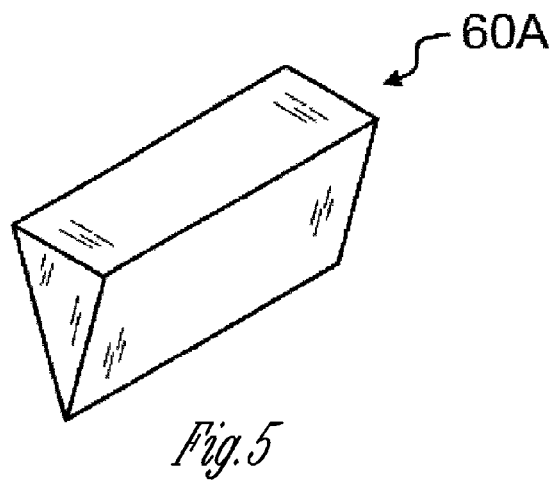
FIG. 5 is a perspective view of an alternative form of a dental wedge, in accordance with at least one example.

FIGS. 5-70 illustrate a variety of dental wedge forms 60A-60NNN. Although each of the wedges 60A-60NNN are depicted as having a certain length relative to its depth and width, it is to be understood that other relative dimensions are contemplated. From various examples described herein, it should be understood that any combination of three-dimensional geometric shapes and two-dimensional facets are possible, even beyond those specifically depicted in FIGS. 5-70. Further, various examples can include one or more 3-D shaped slots (e.g., 72) in the dental wedge. The one or more 3-D slots can be any 3-D shape including, but not limited, to the shape illustrated in the FIGS. Various examples illustrate one or more protrusions (e.g., 71) on a facet of a dental wedge. It should be understood that any combination of 3-D geometric shaped protrusions or number of protrusions are possible, even beyond those specifically depicted in FIGS. 5-70. Further, general families of dental wedge 60 geometries can be combined in any combination. For example, families can include, but are not limited to, solid dental wedges (e.g., FIGS. 5-9), bored dental wedges (e.g., FIGS. 3, 11, 17-18), slot dental wedges (e.g., FIGS. 10, 16, 21, 42), protrusion dental wedges (e.g., FIGS. 30-34), block dental wedges (e.g., FIGS. 25, 27, 42-43), full or partial arched or horseshoe dental wedges (e.g., 46-58), single tooth dental cavity wedges (e.g., FIGS. 13, 15,17-19), multiple tooth dental cavity wedges (e.g., FIGS. 12, 14, 16, 38, 46), wire framed dental wedges (e.g., FIGS. 44, 60, 62, 64), and any combination thereof.

Figure 6:
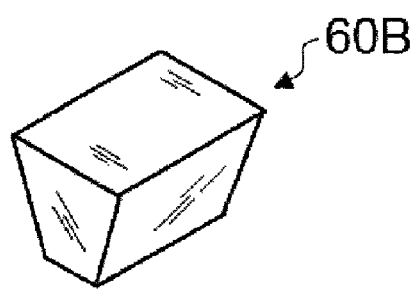
FIG. 6 is a perspective view of an alternative form of a dental wedge, in accordance with at least one example.

FIG. 5 illustrates a dental wedge 60A having a triangular prism shape. The wedge 60A can have a horizontal cross-section, with a rectangular shape; and a vertical cross-section, with a triangular shape. FIG. 6 illustrates a dental wedge 60B having a truncated triangular prism. The wedge 60B has a horizontal cross-section, with a rectangular shape; and a vertical cross-section, with a trapezoidal shape.

Figure 7:
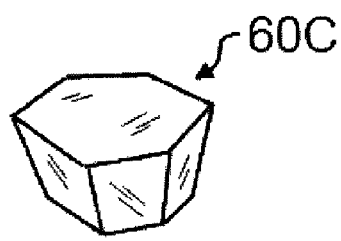
FIG. 7 is a perspective view of an alternative form of a dental wedge, in accordance with at least one example.

FIG. 7 illustrates a dental wedge 60C. The wedge 60C can have a horizontal cross-section, with a hexagonal shape; and a vertical cross section, with a trapezoidal shape. Relative dimensions of each facet again are not limiting, nor the specific shape. For example, while not depicted, the wedge 60C can be cylindrical or cubic in shape, or generally cylindrical or cubic with a diagonally cut plane slicing through and forming its bottom surface (e.g., 60L, FIG. 15).

Figure 8:
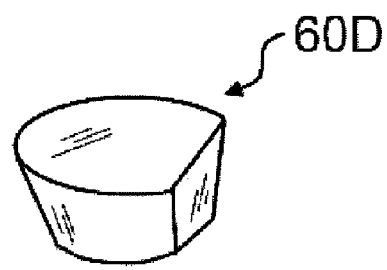
FIG. 8 is a perspective view of an alternative form of a dental wedge, in accordance with at least one example.
Figure 9:
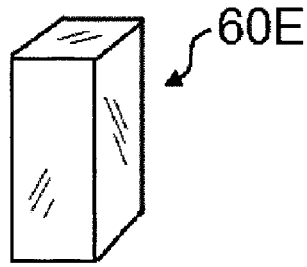
FIG. 9 is a perspective view of an alternative form of a dental wedge, in accordance with at least one example.

FIG. 8, illustrates a dental wedge 60D. The wedge 60D can have a horizontal cross-section, with a truncated oval shape; and a vertical cross-section, with a trapezoidal shape. Although the wedge 60D is depicted as having a certain length relative to its depth and width, it is to be understood that other relative dimensions are possible. FIG. 9 illustrates a dental wedge 60E, which can have a cuboid shape.

Figure 10:
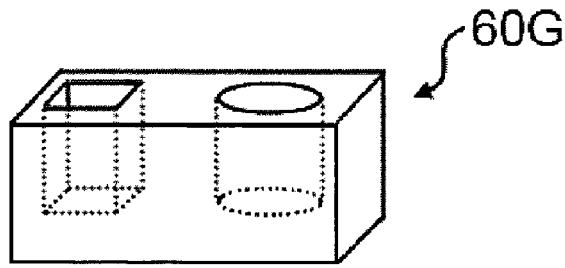
FIG. 10 is a perspective view of an alternative form of a dental wedge, in accordance with at least one example.
Figure 11:
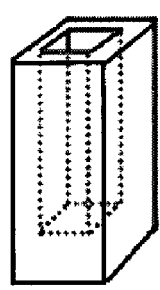
FIG. 11 is a perspective view of an alternative form of a dental wedge, in accordance with at least one example.

FIG. 10 illustrates a dental wedge 60G, which can have a cuboid shape with one or more slots cut into the dental wedge. As shown, the wedge 60G can have a cuboid-shaped slot or a cylinder-shaped slot. In various examples, the dental wedge 60G can have other 3-D shapes of slots. Further, although two slots are shown in the dental wedge 60G other numbers of slots are contemplated. FIG. 11 illustrates a dental wedge 60F. The dental wedge 60F can be a cuboid with a cuboid-shaped slot cut into its material. In various examples, the dental wedge 60F can include any number of 3-D shaped slots.

Figure 12:
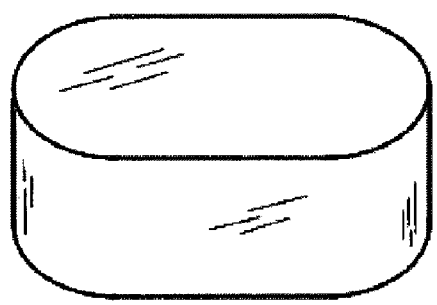
FIG. 12 is a perspective view of an alternative form of a dental wedge, in accordance with at least one example.
Figure 13:
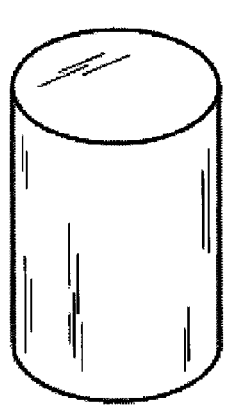
FIG. 13 is a perspective view of an alternative form of a dental wedge, in accordance with at least one example.
Figure 14:
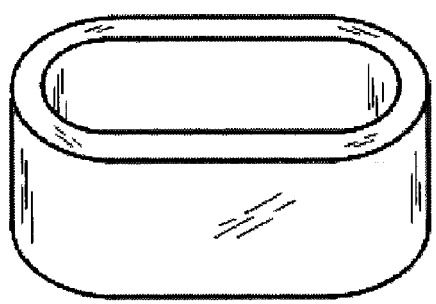
FIG. 14 is a perspective view of an alternative form of a dental wedge, in accordance with at least one example.
Figure 15:
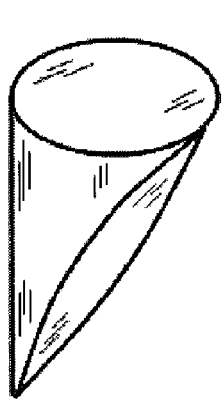
FIG. 15 is a perspective view of an alternative form of a dental wedge, in accordance with at least one example.

FIG. 12 illustrates a dental wedge 60H. Dental wedge 60H can have a horizontal cross-section, with a hollow oval shape; and a vertical cross section, with a rectangular shape. FIG. 13 illustrates a dental wedge 60K, which can have a cylindrical shape. Another embodiment of a dental wedge 60I is shown in FIG. 14. The dental wedge 60I can include a hollow oval block with a hollow oval slot cut into its materials. FIG. 15 illustrates an embodiment of a dental wedge 60L. The dental wedge 60L can include a cylinder with a diagonally cut plane slicing through and forming its bottom surface.

Figure 16:
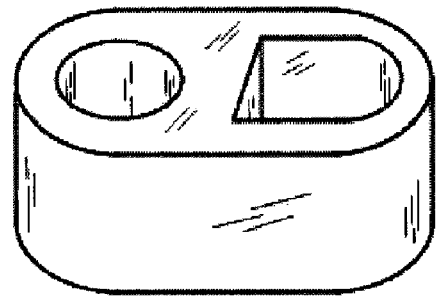
FIG. 16 is a perspective view of an alternative form of a dental wedge, in accordance with at least one example.

FIG. 16 illustrates a dental wedge 60J. The dental wedge 60J can include a hollow oval block with one or more slots cut into its materials. Although the dental wedge 60J is illustrated as having certain 3-D shapes of slots, it is to be understood that other 3-D shapes of slots are possible. Another embodiment of a dental wedge 60M is shown in FIG. 17. The wedge 60M can include a cone with a cone-shaped slot cut into its materials. The slot cut into the dental wedge 60M can include other 3-D shapes.

FIG. 18 illustrates a dental wedge 60N which can include a cylinder with a cylinder-shaped slot cut into its materials. Referring to FIG. 19, another embodiment of a dental wedge 60O includes a cone shape. A dental wedge 60P, illustrated in FIG. 20, can include a pyramid shape. Further, as shown in FIG. 21, a dental wedge 60Q can include a pyramid shape with a 3-D shaped slot cut into its material. For example, the slot can be of a pyramid or other 3-D shape. Referring to FIG. 22, a dental wedge 60R can have a tetrahedron shape.

FIG. 23 illustrates a dental wedge 60S, which can have an arch shape. Although the wedge 60S is shown as having certain relative dimensions, such dimensions are only exemplary and other relative dimensions are possible. For example, the dental wedge 60S can have a length dimension configured to cover or be inserted into one or more dental cavities. FIG. 24 illustrates a dental wedge 60V, which can have an arch shape with one or more slots cut into its materials.

Figure 29:
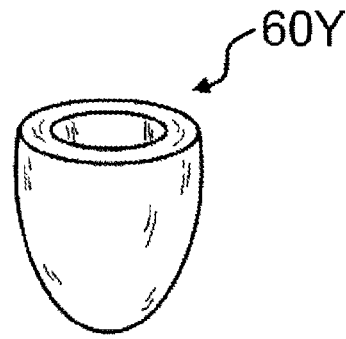
FIG. 29 is a perspective view of an alternative form of a dental wedge, in accordance with at least one example.

FIG. 25 illustrates a dental wedge 60U, which can have a bench shape. Further, FIG. 26 illustrates a dental wedge 60T, which can have a tetrahedron shape with a tetrahedron-shaped slot cut into its materials. Different 3-D slot shapes are contemplated. Turning now to FIG. 27, an embodiment of a dental wedge 60W is shown. The dental wedge 60W can have a bench shape with one or more cylinder-shaped slots cut into its materials on a top face. Referring to FIG. 28, a dental wedge 60X can include a truncated prolate spheroid. FIG. 29 illustrates a dental wedge 60Y which can have a truncated prolate spheroid shape with a slot cut into its materials.

Figure 30:
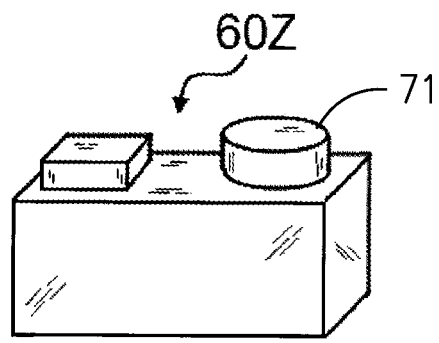
FIG. 30 is a perspective view of an alternative form of a dental wedge, in accordance with at least one example.
Figure 31:
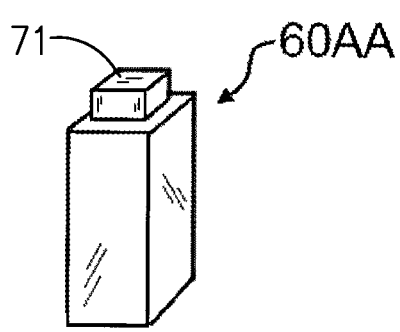
FIG. 31 is a perspective view of an alternative form of a dental wedge, in accordance with at least one example.

FIG. 30 illustrates a dental wedge 60Z. The dental wedge 60Z can have a cuboid shape with one or more protrusions 71 on a top face. As shown, the wedge 60Z can have a cuboid-shaped protrusion 71 or a cylinder-shaped protrusion 71. Referring to FIG. 31, a dental wedge 60AA can have a cuboid shape which has a cuboid-shaped protrusion 71 on a top face.

Figure 32:
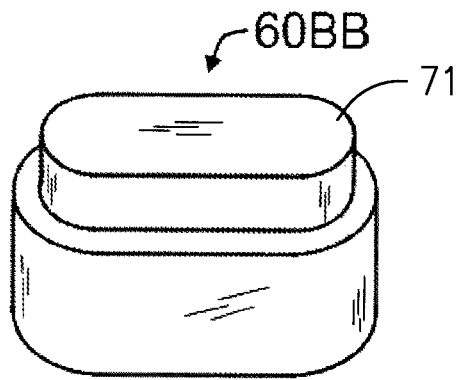
FIG. 32 is a perspective view of an alternative form of a dental wedge, in accordance with at least one example.
Figure 33:
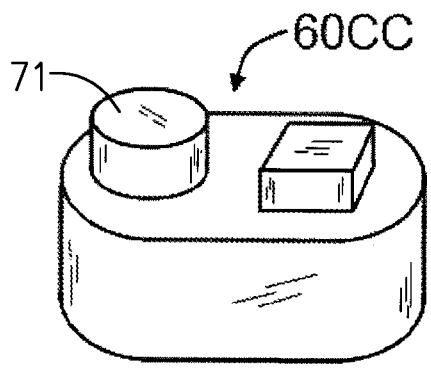
FIG. 33 is a perspective view of an alternative form of a dental wedge, in accordance with at least one example.

As illustrated in FIG. 32, various examples can include a dental wedge 60BB. The wedge 60BB can include a hollow oval block with a hollow oval-shaped protrusion 71 on a top face. Turning now to FIG. 33, an embodiment of a dental wedge 60CC can include a hollow oval block with one or more protrusions 71 on a top face. Various examples that include a plurality of protrusions 71 can include protrusions with the same or different 3-D shape.

Figure 34:
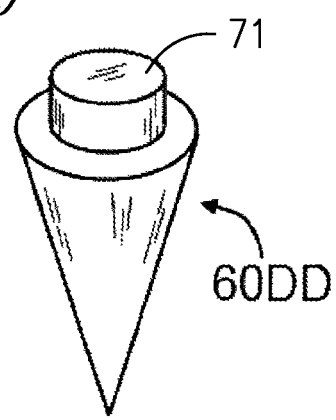
FIG. 34 is a perspective view of an alternative form of a dental wedge, in accordance with at least one example.
Figure 35:
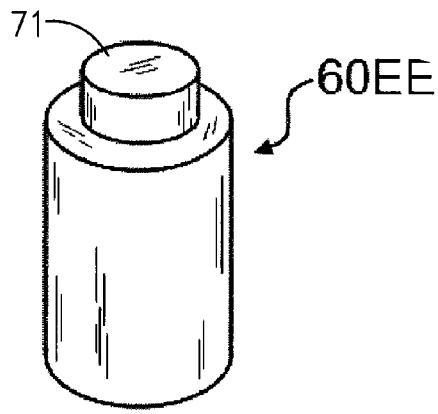
FIG. 35 is a perspective view of an alternative form of a dental wedge, in accordance with at least one example.
Figure 36:
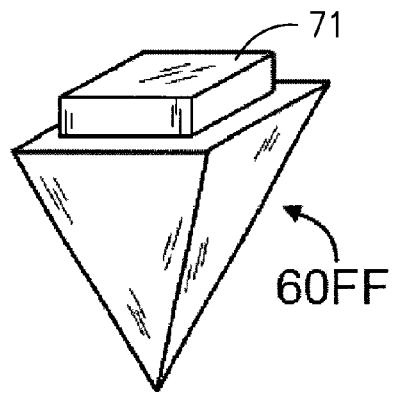
FIG. 36 is a perspective view of an alternative form of a dental wedge, in accordance with at least one example.

FIG. 34 illustrates a dental wedge 60DD which can include a cone with a cylinder-shaped protrusion 71 on a top face. Another embodiment of a dental wedge 60EE is shown in FIG. 35. The dental wedge 60EE can include a cylinder with a cylinder-shaped protrusion 71 on a top face. Turning now to FIG. 36, an embodiment of a dental wedge 60FF can include a pyramid with a cuboid-shaped protrusion 71 on a top face.

Figure 37:
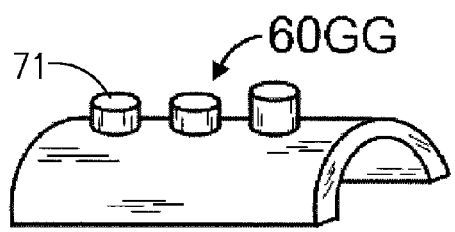
FIG. 37 is a perspective view of an alternative form of a dental wedge, in accordance with at least one example.
Figure 38:
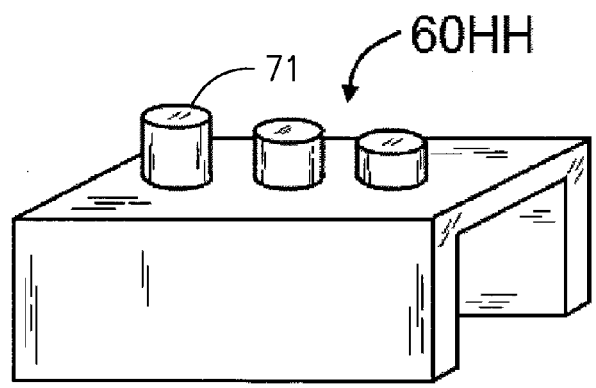
FIG. 38 is a perspective view of an alternative form of a dental wedge, in accordance with at least one example.

Various examples can include a dental wedge 60GG, as shown in FIG. 37. The dental wedge 60GG can include an arch shape with one or more protrusions 71 on a top face. Although the wedge 60GG is depicted as having a certain length relative to its depth and width it is to be understood that other relative dimensions are possible. FIG. 38 shows a dental wedge 60HH which can have a bench shape with one or more protrusions 71 on a top face. Different 3-D shapes or numbers of the protrusions are possible.

Figure 39:
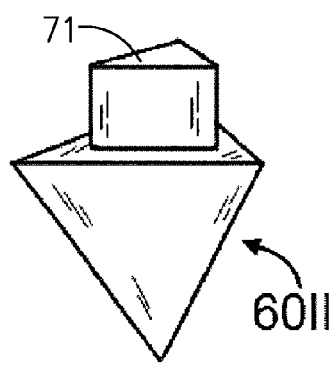
FIG. 39 is a perspective view of an alternative form of a dental wedge, in accordance with at least one example.
Figure 40:
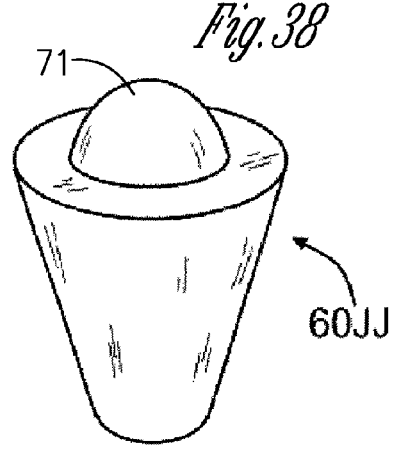
FIG. 40 is a perspective view of an alternative form of a dental wedge, in accordance with at least one example.
Figure 41:
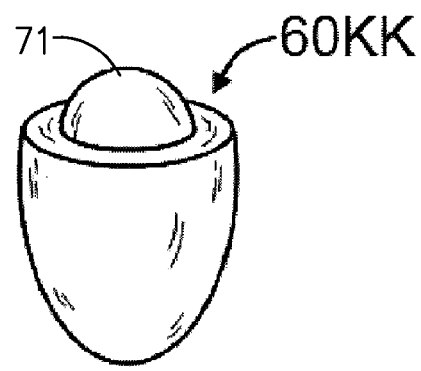
FIG. 41 is a perspective view of an alternative form of a dental wedge, in accordance with at least one example.
Figure 42:
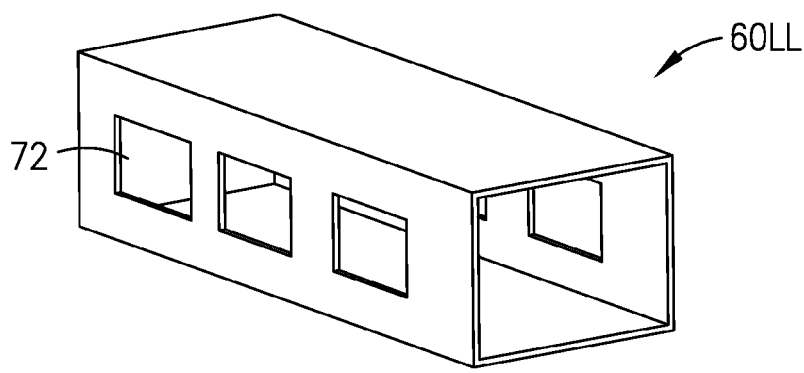
FIG. 42 is a perspective view of an alternative form of a dental wedge, in accordance with at least one example.
Figure 43:
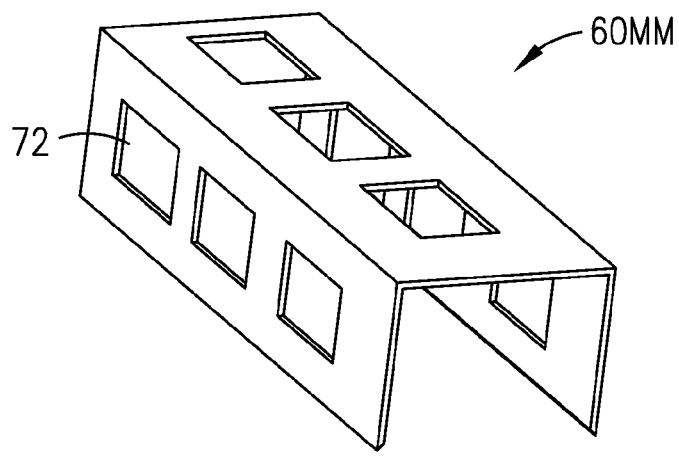
FIG. 43 is a perspective view of an alternative form of a dental wedge, in accordance with at least one example.

Turning now to FIG. 39, an embodiment of a dental wedge 60II is shown. The dental wedge 60II can have a tetrahedron shape with a triangular prism-shaped protrusion 71 on a top face. FIG. 40 illustrates a dental wedge 60JJ, which can include a truncated cone with a truncated sphere-shaped protrusion 71 on a top face. A dental wedge 60KK is illustrated in FIG. 41. The dental wedge 60KK can include a truncated prolate spheroid shape with a truncated sphere-shape protrusion 71 on a top face.

Figure 44:
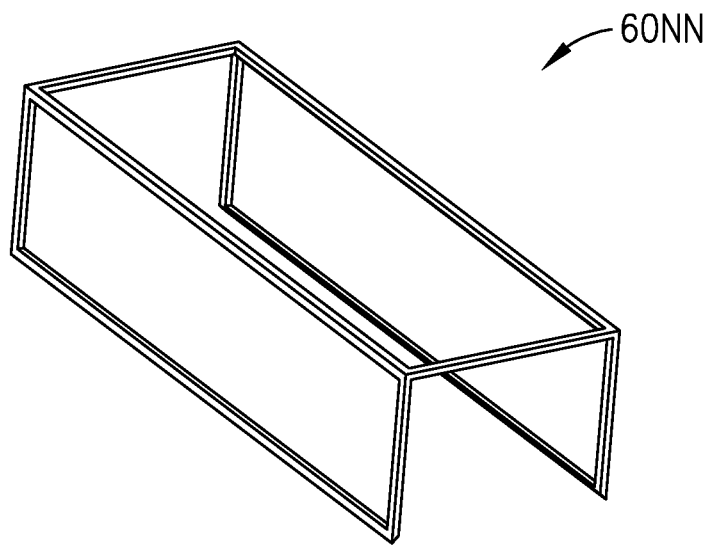
FIG. 44 is a perspective view of an alternative form of a dental wedge, in accordance with at least one example.
Figure 45:
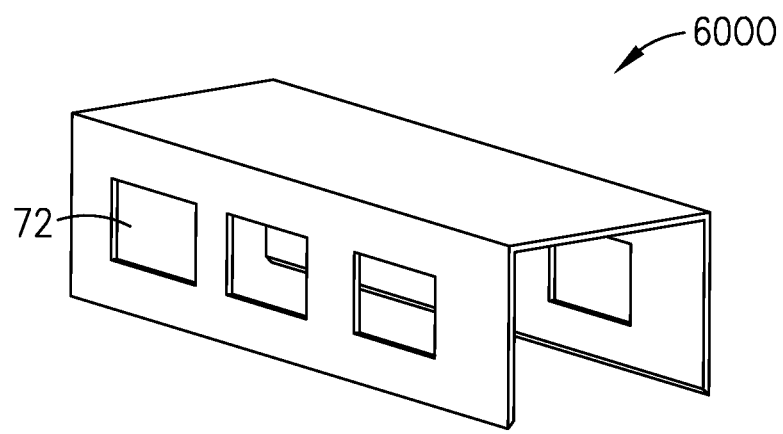
FIG. 45 is a perspective view of an alternative form of a dental wedge, in accordance with at least one example.

FIGS. 42-45 show an embodiment of a bench shaped dental wedge 60LL-60OO. The dental wedge 60LL can have a bench shape, with a bottom surface closing the bench shape to form a rectangular shape. Further, the dental wedge 60LL can include one or more slots 72, such as square slots, cut into its materials on one or more side face. The slots 72 can be coronoally located, such as coronal surface 62 shown in FIG. 3, for instance near a crestal bone, when implanted, and away from the apical end or surface 63 shown in FIG. 3. The dental wedge 60MM, shown in FIG. 43, can include slots 72 on one or more side surfaces and the coronal surface, as described herein. FIG. 44 shows a dental wedge 60NN including a wire framed bench shape, wherein the sides and coronal surface can be removed. The dental wedge 60OO of FIG. 45 can include slots 72 that can be located on one or more surfaces, but not the coronal surface.

Figure 46:
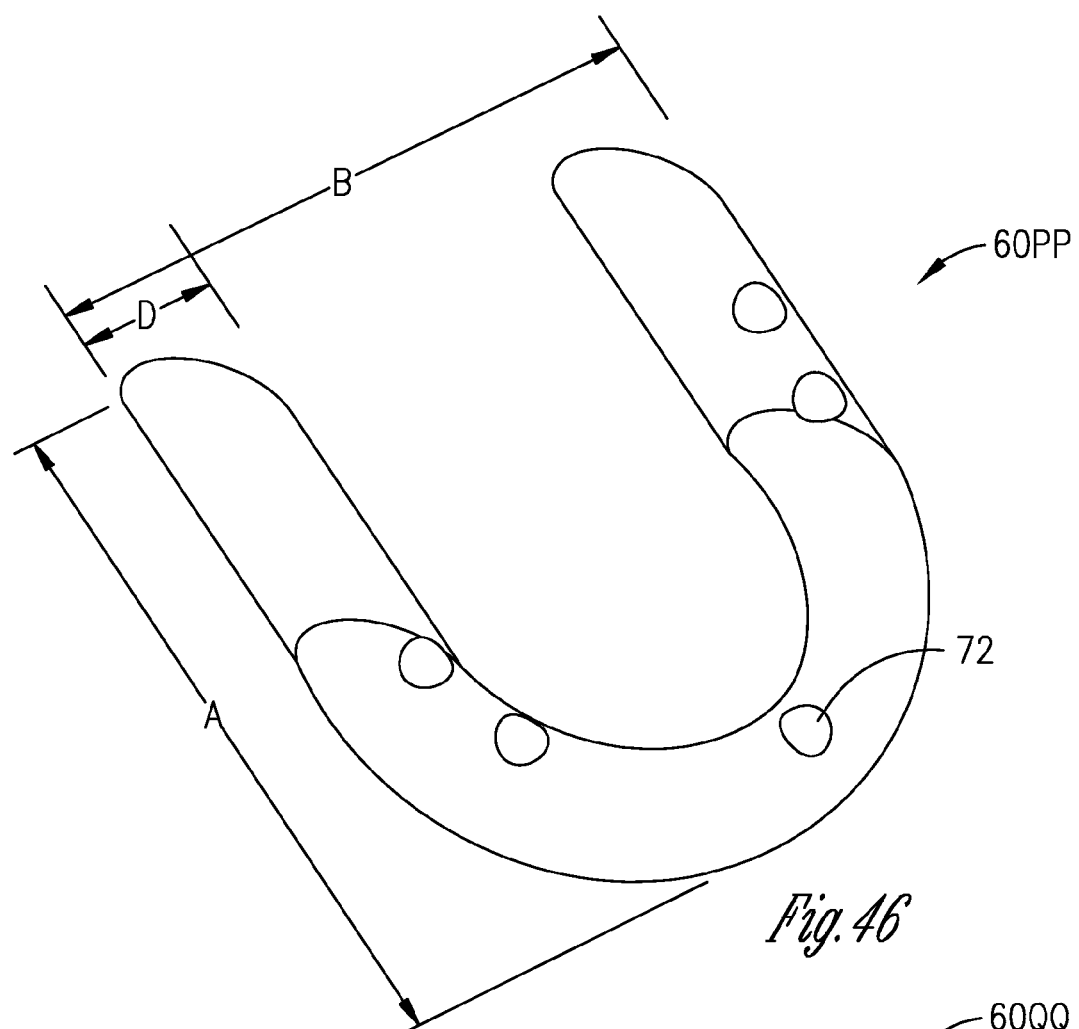
FIG. 46 is a perspective view of an alternative form of a dental wedge, in accordance with at least one example.
Figure 47:
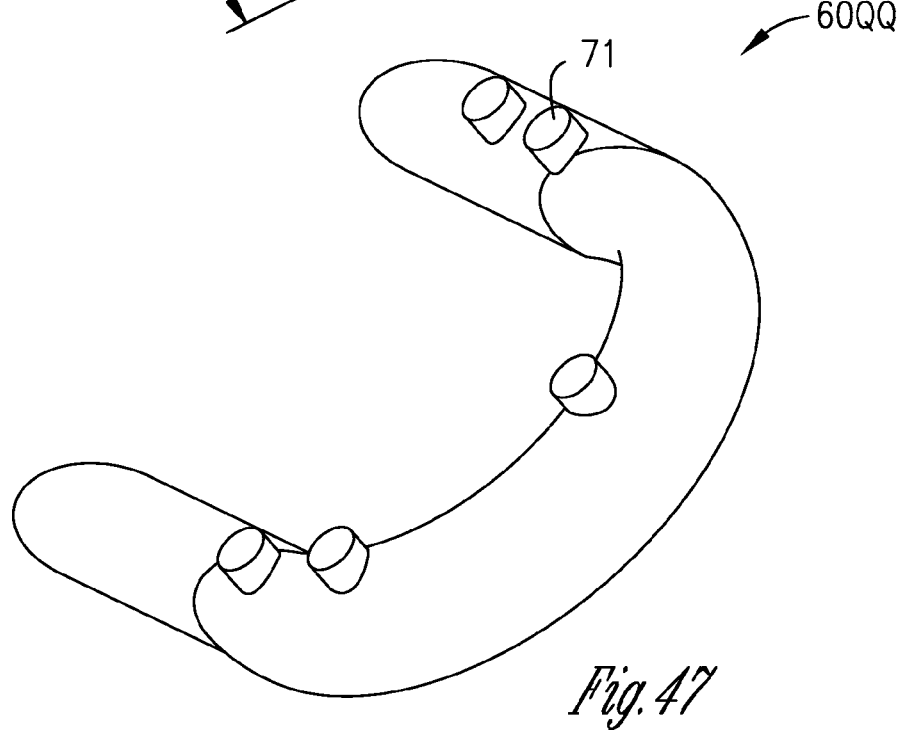
FIG. 47 is a perspective view of an alternative form of a dental wedge, in accordance with at least one example.

FIGS. 46 and 47 illustrate dental wedges 60PP, 60QQ, respectively, having a solid horseshoe or anatomical jaw shape. The horseshoe shape can include an arc segment extended on either end by straight segments. The dental wedges 60PP, 60QQ can have a length A, a width B, and a thickness D. Further, similar horseshow shaped dental wedges can have similar dimensions as shown in FIG. 46. In various examples, the length A can be from about 0.5 mm to about 75 mm, the width B can be from about 0.5 mm to about 80 mm, and the thickness D from about 0.5 mm to about 25 mm, for a mandible full ridge dental wedge. For a maxilla dental wedge, the length A can be from about 0.5 mm to about 70 mm, the width B from about 0.5 mm to about 80 mm, and the thickness D from about 0.5 to 30 mm. The dental wedge 60PP can include slots 72, while the dental wedge 60QQ can include protrusions 71. As illustrated, the dental wedges 60PP, 60QQ are solid but can be hollow in various examples.

Figure 48:
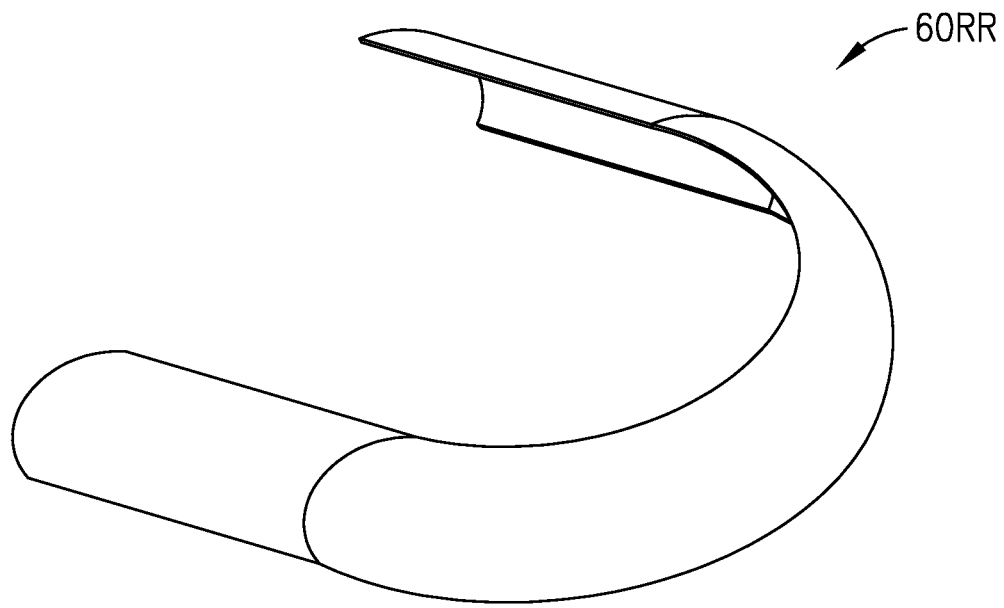
FIG. 48 is a perspective view of an alternative form of a dental wedge, in accordance with at least one example.
Figure 49:
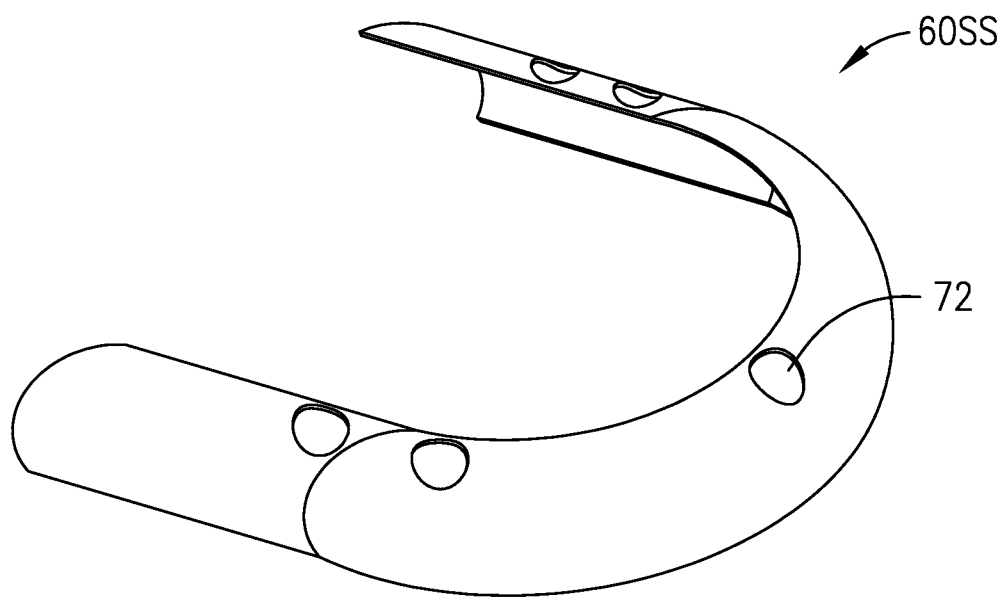
FIG. 49 is a perspective view of an alternative form of a dental wedge, in accordance with at least one example.
Figure 50:
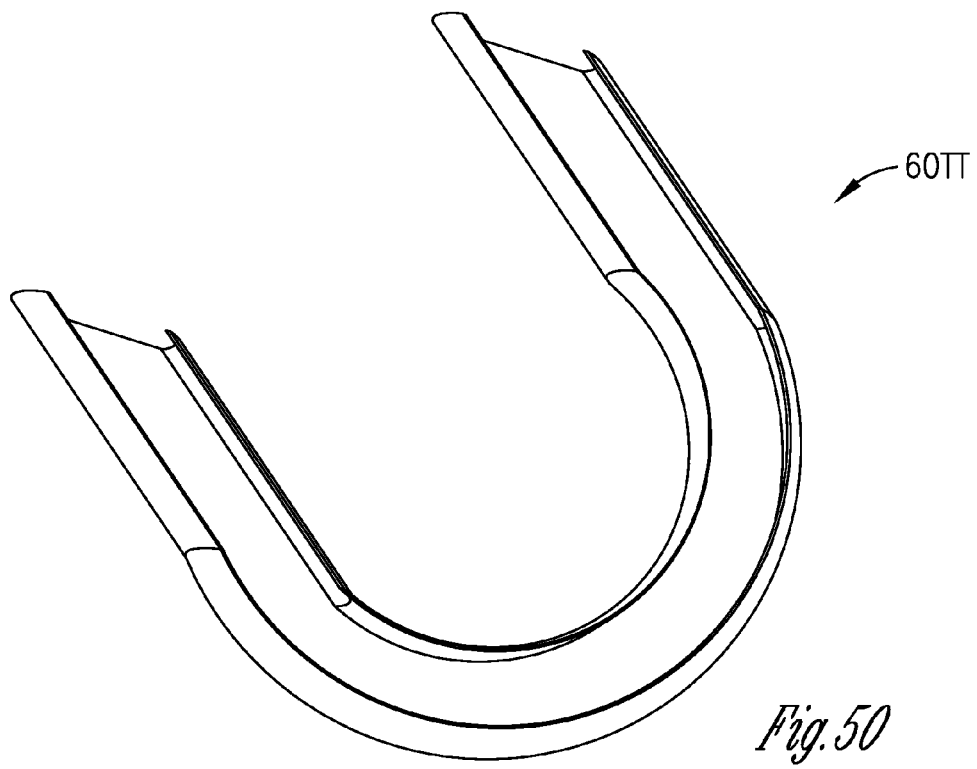
FIG. 50 is a perspective view of an alternative form of a dental wedge, in accordance with at least one example.
Figure 51:
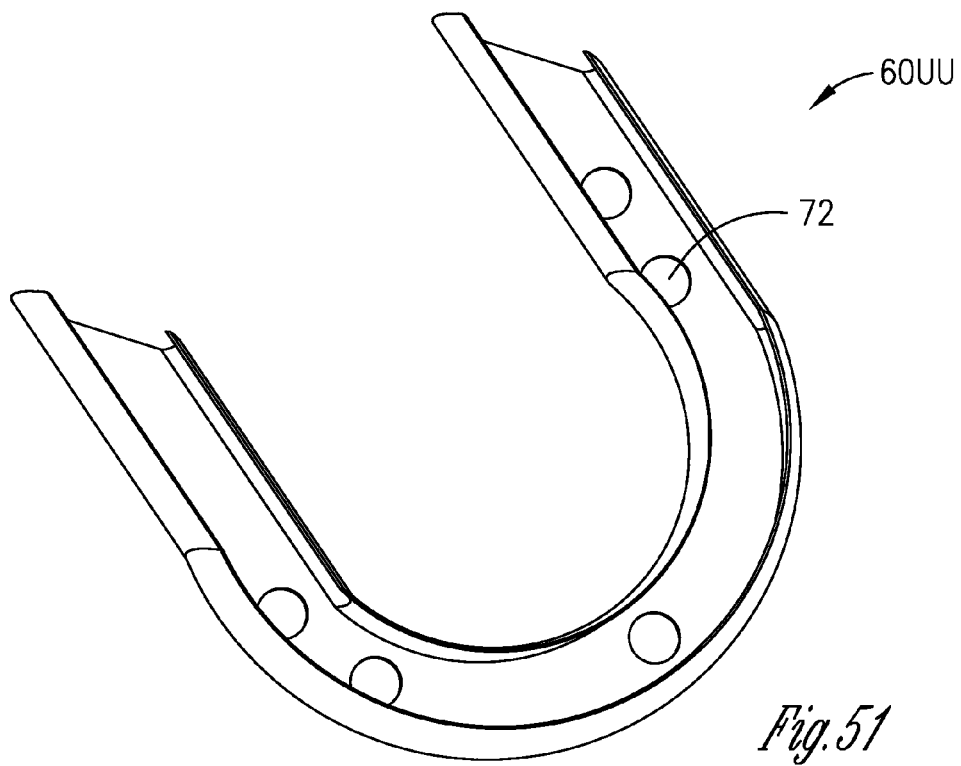
FIG. 51 is a perspective view of an alternative form of a dental wedge, in accordance with at least one example.

FIG. 48 depicts a hollow horseshoe-shaped dental wedge 60RR, while FIG. 49 depicts a hollow horseshoe-shaped dental wedge 60SS having slots 72, wherein the slots can be located anywhere on the horseshoe. Dental wedges 60RR and 60SS can be used for buccal wall and ridge augmentation, such that each dental wedge can be supported by dental bone at a top and front of the jaw. The dental wedges 60TT, 60UU of FIGS. 50 and 51, respectively, are horseshoe shaped and hollow while incorporating a rail or track profile. The rail or track structure can be utilized to grip bone, tissue, or other objects. The dental wedge 60UU can incorporate slots 72.

FIGS. 52 and 53 depict arc-shaped dental wedges 60VV, 60WW. As illustrated, the dental wedges 60VV, 60WW can be approximately one-half of the arc segment 80 of the dental wedges 60PP, 60QQ. In an embodiment, the dental wedges 60VV, 60WW can be solid as depicted but can be hollow in other examples. The dental wedge 60VV can include protrusions 71 while the dental wedge 60WW can include slots 72. The dental wedges 60VV and 60 WW can, for example, be used in a partial ridge augmentation, such that the length A and thickness D of the dental wedge 60PP (FIG. 46) and the width C of the dental wedge 60XX, as discussed in FIG. 54, can be applied to each.

The dental wedges 60XX, 60YY of FIGS. 54 and 55, respectively, can include an arc segment and a straight segment, such that each dental wedge can be used for buccal wall and ridge augmentation, as discussed herein. In an embodiment, the dental wedges 60XX, 60YY can be the dental wedges 60RR, 60SS split length-wise. In an embodiment, the arc segment is half the arc 80. The dental wedges 60XX, 60YY have a length A and a width C. In an embodiment, the width C is about one-half the width B. The dental wedge 60YY can have slots 72.

Figure 56:
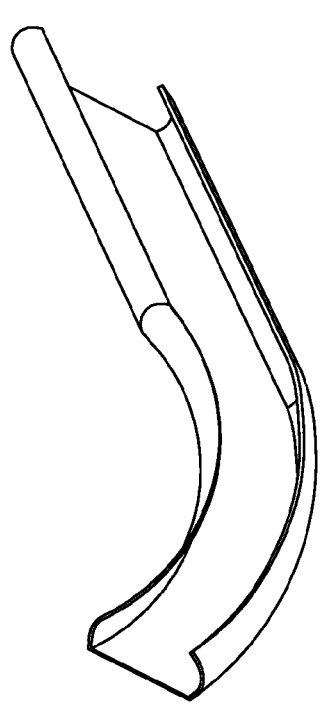
FIG. 56 is a perspective view of an alternative form of a dental wedge, in accordance with at least one example.
Figure 57:
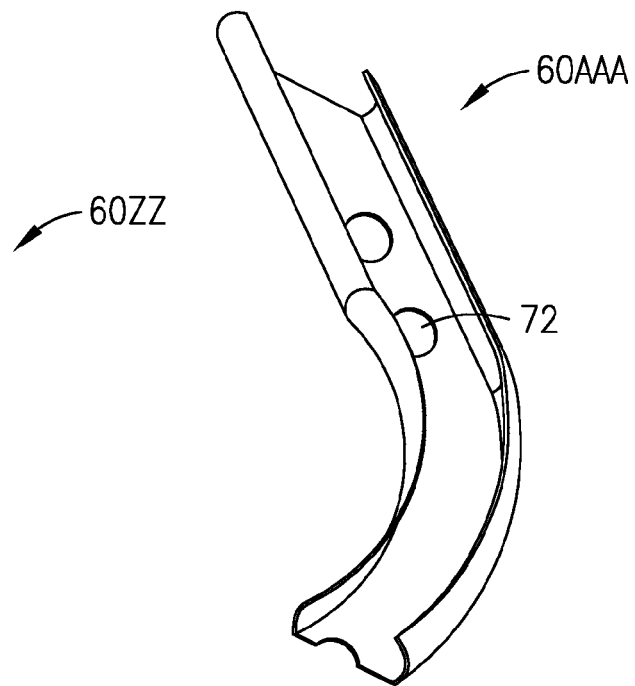
FIG. 57 is a perspective view of an alternative form of a dental wedge, in accordance with at least one example.
Figure 58:
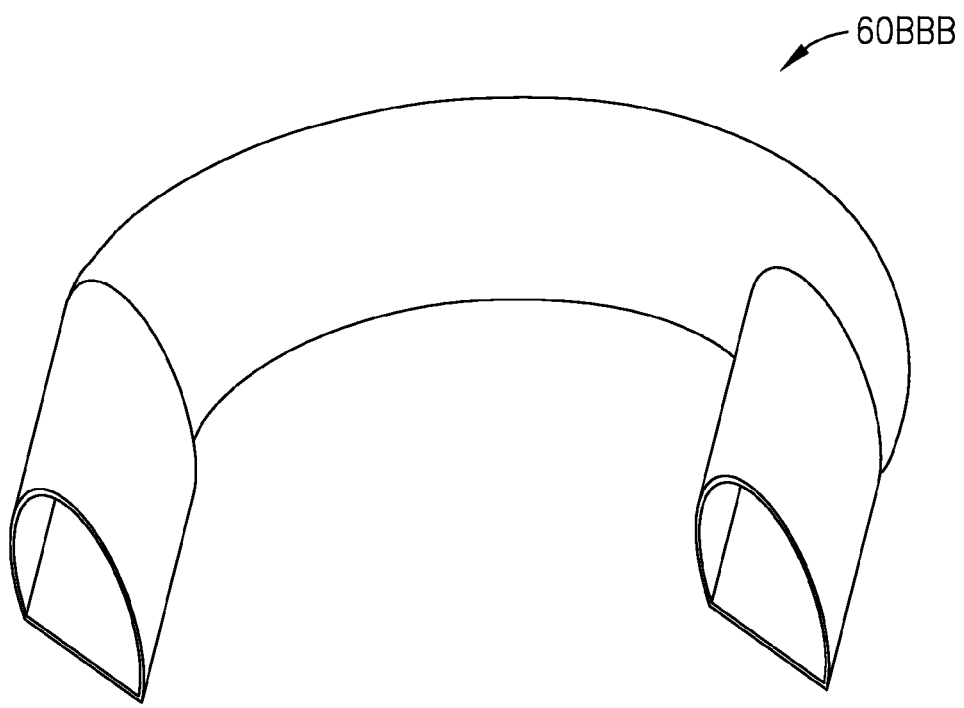
FIG. 58 is a perspective view of an alternative form of a dental wedge, in accordance with at least one example.

FIGS. 56 and 57 show dental wedges 60ZZ, 60AAA, respectively, that are hollow and include a rail or track, so as to be configured for buccal wall and ridge augmentation. The dental wedges 60ZZ, 60AAA can respectively be the dental wedges 60TT, 60UU split length-wise. The dental wedge 60AAA can include slots 72. The dental wedge 60BBB of FIG. 58 is a hollow horseshoe-shape. The hollow cavity can be filled with biomaterial or graft material, such that the dental wedge 60BBB can used for ridge augmentation or ridge bone height preservation or rebuilding.

Figure 59:
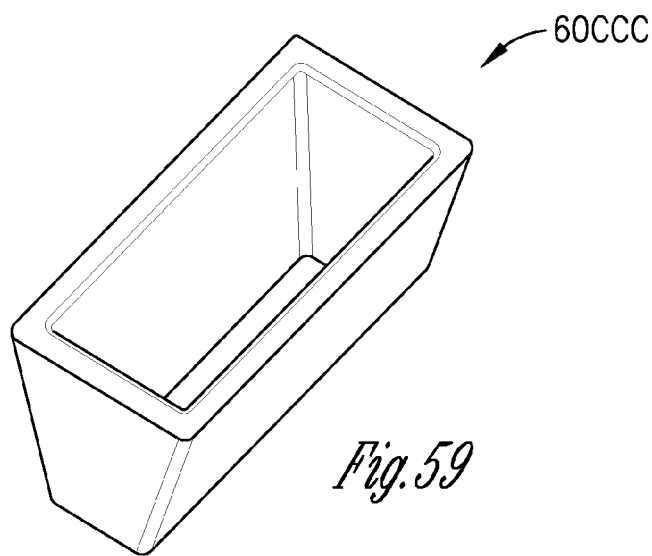
FIG. 59 is a perspective view of an alternative form of a dental wedge, in accordance with at least one example.
Figure 60:
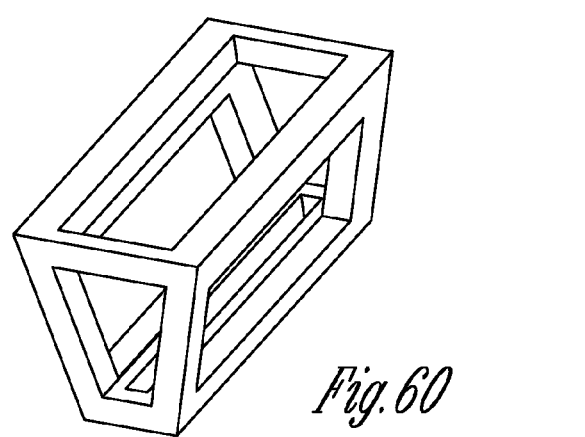
FIG. 60 is a perspective view of an alternative form of a dental wedge, in accordance with at least one example.
Figure 61:
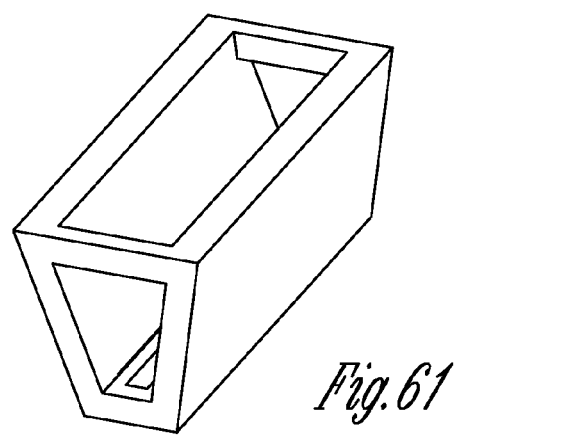
FIG. 61 is a perspective view of an alternative form of a dental wedge, in accordance with at least one example.
Figures 62, 63:
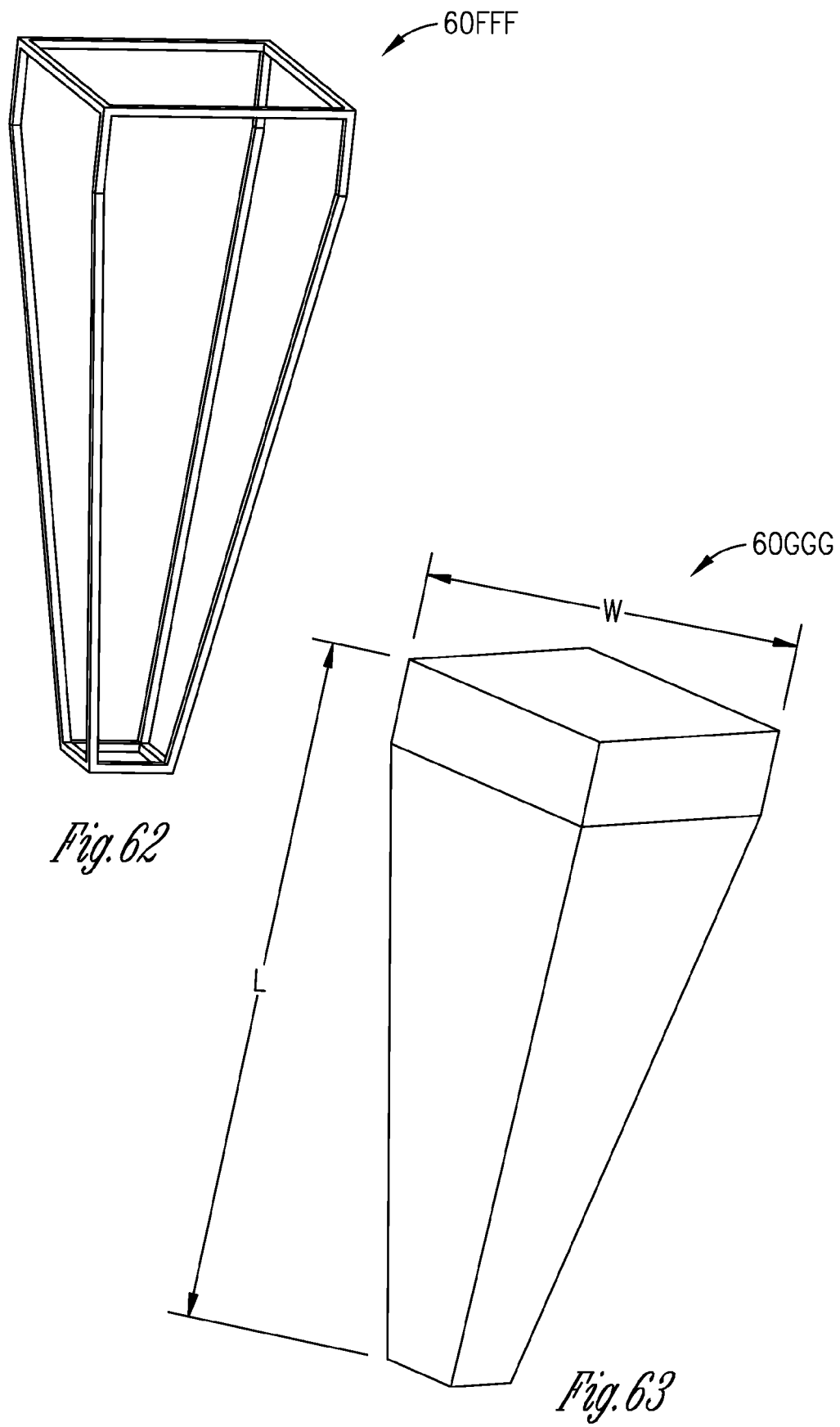
FIG. 62 is a perspective view of an alternative form of a dental wedge, in accordance with at least one example.
FIG. 63 is a perspective view of an alternative form of a dental wedge, in accordance with at least one example.

FIGS. 59-61 illustrate dental wedges 60CCC, 60DDD, 60EEE, respectively, each forming a truncated triangular prism. The wedges 60CCC, 60DDD, 60EEE have a horizontal cross-section, with a rectangular shape; and a vertical cross-section, with a trapezoidal shape. The dental wedge 60CCC forms a bore, with open faces at the coronal and apical ends and solid faces on the four side faces. The dental wedge 60DDD forms a frame, with all faces open. The dental wedge 60EEE forms a bore-frame hybrid, with open faces on the coronal and apical ends, and two sides and solid faces on the remaining two sides. FIGS. 62 and 63 illustrate dental wedges 60FFF, 60GGG, respectively, that combine a cuboid segment at the coronal end with a truncated-pyramid segment at the apical end. As illustrated, the dental wedge 60FFF is a frame while the dental wedge 60GGG is a solid. The dental wedges 60FFF, 60GGG can include a length L and a width W, such the diagonal of the coronal surface. In an embodiment, the width W is a diagonal measurement of the cuboid segment.

Figure 64:
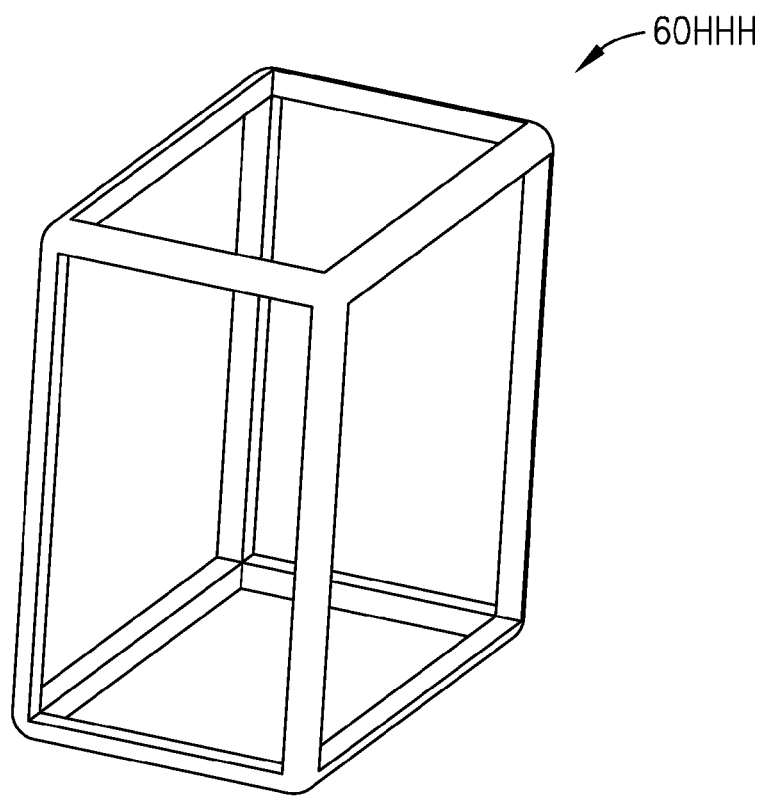
FIG. 64 is a perspective view of an alternative form of a dental wedge, in accordance with at least one example.
Figure 65:
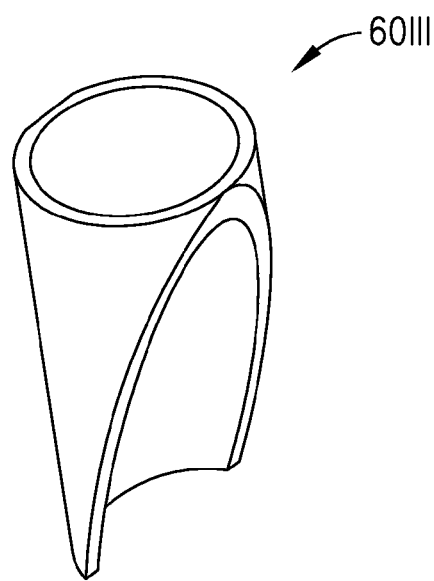
FIG. 65 is a perspective view of an alternative form of a dental wedge, in accordance with at least one example.
Figure 66:
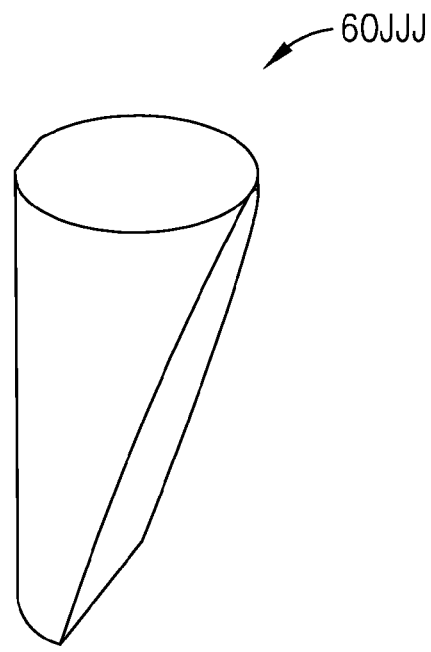
FIG. 66 is a perspective view of an alternative form of a dental wedge, in accordance with at least one example.

FIG. 64 illustrates a dental wedge 60HHH, which can have a cuboid frame. The dental frames 60III, 60JJJ of FIGS. 65 and 66, respectively, can include a cylinder with a diagonally cut plane slicing therethrough and forming their respective bottom surfaces. As illustrated, the dental frame 60III forms a bore while the dental frame 60JJJ forms a solid.

Dental wedges 60KKK, 60LLL, and 60MMM are shown in FIGS. 67-69, respectively. The wedges 60KKK, 60LLL, and 60MMM can form truncated cones. The dental wedge 60KKK forms a frame, the dental wedge 60LLL forms a bore-frame hybrid, with slots cut in the side of the dental wedge 60LLL, and the dental wedge 60MMM forms a bore. FIG. 70 illustrates a dental wedge 60NNN which can include a cylinder frame.

In various examples, a dental wedge of the present disclosure can be configured to be a stand-alone dental implantation system to be inserted into a dental bone cavity without an ensuing insertion of a dental implant. In one embodiment, the dental wedge can be configured to be a stand-alone bone void filler to help the growth of bone tissues at least partially around the dental wedge and promote osseointegration. The bone void could be a cavity formed after an extraction of a tooth or a cavity formed after any other traumas which leave a void in the dental bone structure. In such examples, the dental wedge can include a dental bone augmentation wedge.

According to another embodiment, the dental wedge of the present disclosure can be made of metals, polymers, ceramics, or a combination thereof. The metals can include titanium, trabecular metal, titanium alloy, tantalum, tantalum alloy, cobalt-chrome, or a combination thereof. The polymers can include resorbable polymers or non-resorbable polymers. The ceramics can include resorbable ceramics.

The dental wedge of the present disclosure can include a variety of form configurations. In an embodiment, the dental wedge can include a unitary piece or assembly. In another embodiment, the dental wedge can include a plurality of pieces integrated together. In another embodiment, the dental wedge can remain substantially as one unitary piece after insertion into a dental bone cavity. In still another embodiment, the dental wedge can separate into several pieces after being inserted into the dental bone cavity. In various examples, the dental wedge can include one or more bores in its body. However, a dental wedge according to the present disclosure can include a body without a bore.

A number of factors can be considered when choosing a shape or form of the dental wedge including, but not limited to, characteristics of the dental bone cavity into which the dental wedge is going to be inserted; whether the dental wedge will remain as one piece or break into several pieces after the insertion; what type of dental implant would, if any, be inserted into the dental bone cavity afterwards; whether a shape or form selected would provide better stability for the dental implant; or whether the dental implant can be inserted through or alongside, near, or proximate the dental wedge.

Turning back to FIG. 2, a dental bone augmentation composition 67 can be provided to the dental bone cavity 42 to promote or expedite bone growth toward and at least partially around the dental wedge 60. The bone augmentation composition 67 can include an allograft material. Exemplary allograft materials suitable for use in the present disclosure include, but are not limited to, demineralized bone matrix (DBM) such as DBM sold by Zimmer Dental Inc. under the trademark Puros®, bone morphogenetic protein (BMP), human growth hormone (HGH), other regenerative materials derived from a human body, biomaterial, bone graft material, tissue graft material, such as autograft, allograft, xenograft, alloplast, or mixtures and blends thereof.

The allograft material can be coated, impregnated, supported, or otherwise associated with a resorbable polymer. The term "resorbable", as used herein, refers to a material that maintains its structural integrity during an initial period of time but is capable of being disintegrated and absorbed by a living body afterwards. For example, resorbable polymers suitable for use in the present disclosure can include, but are not limited to, polylactic acid, polyglycolic acid, polycaprolactone, and other biodegradable polymers.

In various examples, the bone augmentation composition 67 can include other ingredients. In one embodiment, the resorbable material can further include an anti-inflammatory medication to expedite healing of the surgically created dental cavity. In another embodiment, the resorbable or non-resorbable but biocompatible material can further include an imaging agent, such as barium sulfate, so that the radio-opaque material can be readily locatable by X-ray.

The bone augmentation composition 67 can be delivered to the dental bone cavity 42 in a semi-solid state to facilitate bone growth toward or at least partially around the dental wedge 60. For example, the bone augmentation composition 67 can be introduced into the dental bone cavity 42 through injection or puttying. In one embodiment, the bone augmentation composition 67 can delivered to the dental bone cavity 42 via an injection gun with a nozzle. In another embodiment, the resorbable material can be forced with fingers or surgical tools into the dental cavity 42 in putty form.

After application, the bone augmentation composition 67 can promote or expedite bone growth toward or at least partially around the dental wedge 60. In addition, the resorbable material of the bone augmentation composition 67 can provide high initial stability to a dental wedge-bone interface or act to resist tensile forces, compressive forces, or bending and twisting forces generated by the chewing motion of jaw bones. It is contemplated that the resorbable material can also act as a medium for rapid in-growth of bone at least partially around or into the dental wedge 60.

In various examples, after sufficient bone growth toward or at least partially around the dental wedge 60, the dental implant 21 can be inserted through the dental wedge 60 and into the dental bone cavity 42. A wedge locator can be provided to determine a relative position of the dental wedge 60 within the dental bone cavity 42.

In an embodiment, the wedge locator can be an X-ray apparatus commonly available to dental surgeons. For example, after sufficient bone augmentation, the surgeon can take an X-ray of the dental bone cavity 42 with the dental wedge 60 disposed therein. The surgeon can then use experience to select a drilling location or create an osteotomy at the dental bone cavity 42 according to the X-ray images. In a refinement, the surgeon can take measurements from the X-ray images. Thereafter, the surgeon can create an osteotomy at the dental bone cavity 42 according to measurements.

In another embodiment, the wedge locator can be a computed tomography (CT) or a cone beam computed tomography (CBCT) scanner, in which case the surgeon can take a CT or CBCT scan of the dental bone cavity 42 after sufficient bone augmentation around the dental wedge 60. The surgeon can then use experience to select a drilling location or create an osteotomy at the dental bone cavity 42 according to the CT or CBCT scans, or the surgeon can take measurements from the CT or CBCT scans or create an osteotomy at the dental bone cavity 42 according to measurements.

To further facilitate the insertion of the dental implant 21 through the dental wedge 60 and into the dental bone cavity 42, the surgeon can take an impression surrounding the dental bone cavity 42 and have a surgical drill guide fabricated according to the impression and the location of the dental wedge 60 within the dental bone cavity 42 obtained through the wedge locator. In a refinement, when the wedge locator is a CT or CBCT scanner, the surgeon can plan the case using a commercially available case planning software tool for implant placement and have a guide fabricated accordingly to create the osteotomy at the planned location.

One feature of the present disclosure is improved securement and stability of the dental implant 21 within the dental bone cavity 42. It is contemplated that the one or more structural features of the dental wedge 60, alone or in combination, can contribute to the securement and stability of the dental wedge 60 within the dental bone cavity 42. Such structural features can include, but are not limited to, the shape of the dental wedge 60, the dimension of the dental wedge 60, the material of the dental wedge 60, or porous surface character of the dental wedge 60. The various shapes of the dental wedge 60 can be included in a kit which can be used to fit patient and surgical needs. When the dental implant 21 and the dental wedge 60 are fixedly attached together, the structural features or other beneficial effects of the dental wedge 60 according to the present disclosure can also contribute to the stability of the implant 21 within the dental bone cavity 42. When the dental implant 21 and the dental wedge 60 are not attached together, the presence of the dental wedge can still provide beneficial effects due its promotion of stabilization within the dental cavity 42.

While the implant 21 is shown herein as being centered within the dental wedge 60, this need not be the case. In various examples, the implant 21 can penetrate through another portion of the dental wedge 60, at an angle to or parallel with the longitudinal axis of the dental wedge 60. The implant 21, in some examples, need not touch the dental wedge 60, rather the dental wedge 60 can be in the vicinity of the implant 21 to capitalize on enhanced tissue growth properties of the dental wedge 60, thus making for a more secure installation. In examples where the implant 21 penetrates the dental wedge 60, the dental wedge 60 can split.

While not depicted, this can cause two or more portions of the dental wedge 60 to be formed. This too may augment the ability of the implant 21 to find a secure fitment in that the dental wedge 60 can promote late tissue growth or, due to the split, provide or maintain space to ensure a better securement as well.

The above Detailed Description includes references to the accompanying drawings, which form a part of the Detailed Description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other examples can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or examples, with each claim standing on its own as a separate embodiment, and it is contemplated that such examples can be combined with each other in various combinations or permutations. The scope of the invention should be determined with reference to the appended claims, along with the full scope of equivalents to which such claims are entitled.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims.

What is claimed is:

1. A dental implantation system, comprising:
a plurality of dental wedges including at least one of the plurality of dental wedges having one or more of a porous surface character, an outer frame with an open inner cavity, and a configuration that separates into several pieces after implantation, each of the dental wedges having a variety of differing form configurations having a geometric shape that is configured to correspond to at least one of the plurality of differently shaped dental bone cavities, each dental wedge including a securement feature configured to secure at least an apical end portion of a dental implant, the geometric shape of each dental wedge of the plurality of dental wedges corresponding to a shape of the at least one of the plurality of dental bone cavities such that the geometric shape of the dental wedge is maintained at insertion, and at least one of the dental wedges of the plurality of dental wedges maintains a space within the dental bone cavity for the dental implant.

2. The system of claim 1, further comprising:
a wedge locator adapted to locate a dental wedge of the plurality of dental wedges within the dental bone cavity, wherein the wedge locator is selected from the group consisting of X-ray apparatuses, CT scanners, and CBCT scanners; and
a dental implant adapted to be inserted into the dental bone cavity.

3. The system of claim 1, further comprising a dental bone augmentation composition adapted to allow bone tissues to grow toward and at least partially surround a selected dental wedge of the plurality of dental wedges.

4. The system of claim 3, wherein the dental bone augmentation composition comprises a bone graft material.

5. The system of claim 1, further comprising a guide operatively associated with the dental implant, the guide corresponding to the location of a selected dental wedge of the plurality of dental wedges and adapted to align the dental implant with the dental wedge.

6. The system of claim 1, wherein each dental wedge of the plurality of dental wedges is made of a biocompatible material, the biocompatible material comprising at least one of a polymer, a ceramic, titanium, trabecular metal, titanium alloy, tantalum, tantalum alloy, and cobalt-chrome.

7. The system of claim 1, wherein at least one of the dental wedges of the plurality of dental wedges comprises a center bore.

8. The system of claim 1, wherein the dental implant is inserted proximate a selected dental wedge of the plurality of dental wedges.

9. The system of claim 1, wherein the dental implant is inserted into a selected dental wedge of the plurality of dental wedges.

10. The system of claim 1, wherein at least one of the dental wedges of the plurality of dental wedges has a circular cross-section at a coronal end and a non-circular cross-section at an apical end.

11. The system of claim 1, wherein at least one of the dental wedges of the plurality of dental wedges has an arc-shaped geometry.

12. A dental implantation system, comprising:
a plurality of dental wedges including at least one of the plurality of dental wedges having one or more of a porous surface character, an outer frame with an open inner cavity, and a configuration that separates into several pieces after implantation, each of the dental wedges having a variety of differing form configurations having a geometric shape that is configured to correspond to at least one of the plurality of differently shaped dental bone cavities, each dental wedge including a securement feature configured to secure at least an apical end portion of a dental implant, the geometric shape of each dental wedge of the plurality of dental wedges corresponding to a shape of the at least one of the plurality of dental bone cavities such that the geometric shape of the dental wedge is maintained at insertion, wherein after a selected dental wedge of the plurality of dental wedges is inserted, the dental wedge changes to a form which provides enhanced stability for the dental implant.

* * * * *